United States Patent
McCord et al.

(10) Patent No.: US 10,907,203 B1
(45) Date of Patent: Feb. 2, 2021

(54) DNA METHYLATION ASSAYS FOR BODY FLUID IDENTIFICATION

(71) Applicants: Bruce McCord, Miami, FL (US); Hussain Alghanim, Miami, FL (US)

(72) Inventors: Bruce McCord, Miami, FL (US); Hussain Alghanim, Miami, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 0 days.

(21) Appl. No.: 16/901,763

(22) Filed: Jun. 15, 2020

Related U.S. Application Data

(62) Division of application No. 16/712,411, filed on Dec. 12, 2019, now Pat. No. 10,704,089.

(51) Int. Cl.
  *C12Q 1/68* (2018.01)
  *C12Q 1/686* (2018.01)
  *C12Q 1/6806* (2018.01)

(52) U.S. Cl.
  CPC ........... *C12Q 1/686* (2013.01); *C12Q 1/6806* (2013.01); *C12Q 2600/154* (2013.01)

(58) Field of Classification Search
  None
  See application file for complete search history.

(56) References Cited

U.S. PATENT DOCUMENTS

2019/0112659 A1* 4/2019 Carrell ............... C12Q 1/6883

OTHER PUBLICATIONS

Joehanes, Roby et al., entitled "Epigenetic Signatures of Cigarette Smoking," Circ Cardiovasc Genet (Oct. 2016), pp. 436-447.
Park, Jong-Lyul et al., entitled "Identification of body fluid-specific DNA methylation markers for use in forensic science," Forensic Science International: Genetics 13:147-153, 2014.

* cited by examiner

*Primary Examiner* — Aaron A Priest
(74) *Attorney, Agent, or Firm* — Saliwanchik, Lloyd & Eisenschenk

(57) ABSTRACT

The invention pertains to analyzing the DNA methylation levels at specific genetic loci. The DNA methylation levels at the specific genetic loci can be used to detect the presence in a sample of a specific body fluid, for example, semen containing sperm, saliva, or blood. Particularly, the DNA methylation levels at the genetic loci corresponding to SEQ ID NOs: 1, 7, 13, and 19 are used to detect sperms, saliva or blood cells. The DNA methylation levels at the specific loci can be determined by high-resolution melt (HRM) analysis or sequencing of the amplicons produced using specific primers designed to amplify the specific loci. Kits containing the primers and reagents for carrying out the methods disclosed herein are also provided.

20 Claims, 5 Drawing Sheets
(5 of 5 Drawing Sheet(s) Filed in Color)
Specification includes a Sequence Listing.

DNA METHYLATION ASSAYS FOR BODY FLUID IDENTIFICATION

CROSS-REFERENCE TO A RELATED APPLICATION

This application is a divisional application of U.S. Ser. No. 16/712,411, filed Dec. 12, 2019, which is incorporated herein by reference in its entirety.

SEQUENCE LISTING

The Sequence Listing for this application is labeled "SeqList-ST25," which was created on Dec. 12, 2019, and is 8 KB. The Sequence Listing is incorporated herein by reference in its entirety.

BACKGROUND OF THE INVENTION

Human body fluids such as blood, saliva, semen, or sweat are commonly encountered at crime scenes. Determination of the type and origin of body fluids can provide valuable insights into the circumstances leading to the deposition of the DNA evidence at the crime scene. Body fluids are also very useful in crime scene reconstruction. Currently, body fluid identification relies on serological or immunological methods that are based on colorimetric detection of protein markers. Because of the unspecific presence of many of these markers in different body fluids, several of the current methods are presumptive and cannot confirm the presence of the suspected body fluids. In addition, some of the methods may require a large sample and even destroy the sample during testing, both of which are impractical for forensic specimens.

BRIEF SUMMARY OF THE INVENTION

In contrast to the conventional methods, the instant invention provides DNA methylation markers that provide highly tissue specific and sensitive analysis for identification of source body fluids, particularly, semen containing sperms, saliva, and blood. These methylation markers can also be used to determine the origins of the DNA samples, either from a single or multiple sources. In certain embodiments, the methods disclosed herein can be used for the identification of semen containing sperms, saliva, and blood using pyrosequencing and/or high-resolution melt (HRM) analysis. Thus, the invention provides methods that avoid the problems and difficulties associated with the current methods of detecting body fluids, particularly, forensic samples.

In one embodiment, the body fluid and/or cells present in a sample comprise semen or sperm, saliva or buccal epithelial cells, and/or blood or blood cells.

Assays for determining the DNA methylation levels at specific loci in the genomic DNA isolated from a sample are provided. In certain embodiments, the assays comprise HRM analysis or pyrosequencing of amplicons produced using specific primers designed to amplify specific genetic loci in the genomic DNA. Kits containing primers and reagents for performing the methods disclosed herein are also provided.

BRIEF DESCRIPTION OF THE FIGURES

The patent or application file contains at least one drawing executed in color. Copies of this patent or patent application publication with color drawing(s) will be provided by the Office upon request and payment of the necessary fee.

BRIEF DESCRIPTION OF SEQUENCES

Figure 1:
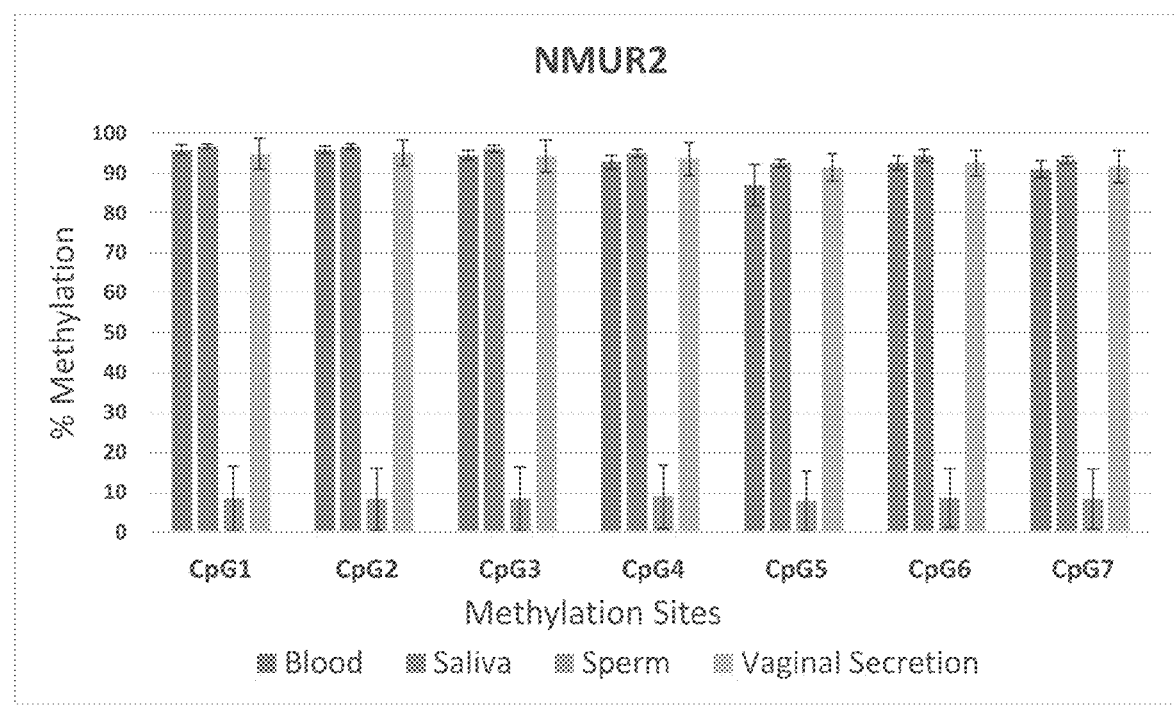
FIG. 1 provides a chart showing the mean percent of methylation on the NMUR2 locus determined by pyrosequencing for samples of blood (n=23), saliva (n=24), sperm (n=20), and vaginal secretion (n=22), ±standard deviation of the mean.

SEQ ID NO: 1: Sequence of the NMUR2 locus specific for sperm.

SEQ ID NO: 2: Sequence of a forward primer designed to amplify the bisulfite treated NMUR2 locus.

SEQ ID NO: 3: Sequence of a reverse primer designed to amplify the bisulfite treated NMUR2 locus.

SEQ ID NO: 4: Sequence of a sequencing primer designed to sequence the amplicon produced from the bisulfite treated NMUR2 locus.

SEQ ID NO: 5: Sequence of the amplicon produced from the NMUR2 locus after bisulfite treatment assuming 0% methylation of all CpG sites. All cytosines, including cytosines from CpG sites are converted to thymines.

SEQ ID NO: 6: Sequence of the amplicon produced from the NMUR2 locus after bisulfite treatment assuming 100% methylation of all CpG sites. Cytosines other than the cytosines from the CpG sites are converted to thymines. Cytosines from the CpG sites remain as cytosines.

SEQ ID NO: 7: Sequence of the UBE2U locus specific for sperm.

SEQ ID NO: 8: Sequence of a forward primer designed to amplify the bisulfite treated UBE2U locus.

SEQ ID NO: 9: Sequence of a reverse primer designed to amplify the bisulfite treated UBE2U locus.

SEQ ID NO: 10: Sequence of a sequencing primer designed to sequence the amplicon produced from the bisulfite treated UBE2U locus.

SEQ ID NO: 11: Sequence of the amplicon produced from the UBE2U locus after bisulfite treatment assuming 0% methylation of all CpG sites. All cytosines, including cytosines from CpG sites are converted to thymines.

SEQ ID NO: 12: Sequence of the amplicon produced from the UBE2U locus after bisulfite treatment assuming 100% methylation of all CpG sites. Cytosines other than the cytosines from the CpG sites are converted to thymines. Cytosines from the CpG sites remain as cytosines.

SEQ ID NO: 13: Sequence of the AHRR locus specific for blood.

SEQ ID NO: 14: Sequence of a forward primer designed to amplify the bisulfite treated AHRR locus.

SEQ ID NO: 15: Sequence of a reverse primer designed to amplify the bisulfite treated AHRR locus.

SEQ ID NO: 16: Sequence of a sequencing primer designed to sequence the amplicon produced from the bisulfite treated AHRR locus.

SEQ ID NO: 17: Sequence of the amplicon produced from the AHRR locus after bisulfite treatment assuming 0% methylation of all CpG sites. All cytosines, including cytosines from CpG sites are converted to thymines.

SEQ ID NO: 18: Sequence of the amplicon produced from the AHRR locus after bisulfite treatment assuming 100% methylation of all CpG sites. Cytosines other than the cytosines from the CpG sites are converted to thymines. Cytosines from the CpG sites remain as cytosines.

SEQ ID NO: 19: Sequence of the SA-6 locus specific for buccal epithelial cell.

SEQ ID NO: 20: Sequence of a forward primer designed to amplify the bisulfite treated SA-6 locus.

SEQ ID NO: 21: Sequence of a reverse primer designed to amplify the bisulfite treated SA-6 locus.

SEQ ID NO: 22: Sequence of a sequencing primer designed to sequence the amplicon produced from the bisulfite treated SA-6 locus.

SEQ ID NO: 23: Sequence of the amplicon produced from the SA-6 locus after bisulfite treatment assuming 0% methylation of all CpG sites. All cytosines, including cytosines from CpG sites are converted to thymines.

SEQ ID NO: 24: Sequence of the amplicon produced from the SA-6 locus after bisulfite treatment assuming 100% methylation of all CpG sites. Cytosines other than the cytosines from the CpG sites are converted to thymines. Cytosines from the CpG sites remain as cytosines.

DETAILED DESCRIPTION OF THE INVENTION

DNA methylation is one of the epigenetic mechanisms for gene regulation. Different DNA methylation levels in certain genetic loci control gene expression by silencing or activating specific genes. The presence of a methyl group on the 5' carbon of a cytosine belonging to the dinucleotide CG (CpG) is believed to prevent the binding of the transcription machinery to the promoter of a gene.

DNA methylation levels at specific genetic loci are different for certain cells from a body fluid when compared to other cells. For example, DNA methylation levels at specific genetic loci are different among the cells from blood, vaginal secretions, saliva, or semen. Accordingly, certain embodiments of the invention provide materials and methods for detecting body fluids in a sample, for example, a forensic sample, based on DNA analyses of the cells present in the sample.

The nucleotide coordinates for genetic loci mentioned herein correspond to University of California Santa Cruz genome browser and Assembly hg19 (UCSC Human Genome Browser GRCh37/hg19 Assembly).

Two genetic loci, namely NMUR2 and UBE2U, are provided that are specific for sperm. The DNA methylation levels at these genetic loci in the genomic DNA obtained from a sperm are significantly different from the DNA methylation levels at these genetic loci in the genomic DNA obtained from the cells from other body fluids, such as blood, vaginal secretions, saliva, and seminal fluid with no sperms. The assays developed using the NMUR2 and/or UBE2U genetic loci can be used in combination with pyrosequencing and/or HRM analysis to determine the DNA methylation levels at these loci.

One marker, namely, SA-6, is provided that is specific for cells in saliva, particularly, buccal epithelial cells, and can be used to identify buccal epithelial cells from the cells obtained from other body fluids, such as semen, vaginal secretions, and blood. Buccal epithelial cells show a significantly different DNA methylation level at the SA-6 genetic locus when compared to the DNA methylation level at this genetic locus in the genomic DNA of the cells obtained from other body fluids.

One marker, namely, AHRR, is provided that is specific for blood cells and can be used to identify blood cells from the cells obtained from other body fluids, such as semen, vaginal secretions, and saliva. Blood cells show a significantly different DNA methylation level at the AHRR genetic locus when compared to the DNA methylation level at this genetic locus in the genomic DNA of the cells obtained from other body fluids.

In certain embodiments, identifying a sperm based on the methods provided herein is performed by determining the DNA methylation level at the sperm specific genetic locus, the NMUR2 locus. Determining the DNA methylation level at the NMUR2 locus can be performed through the use of a specific primer pair that amplifies from the bisulfite-treated genomic DNA at the NMUR2 locus, which has the sequence of SEQ ID NO: 1 in the genomic DNA not treated with bisulfite. An amplicon corresponding to the NMUR2 locus can be obtained by PCR using the bisulfite-treated genomic DNA as a template and a primer pair comprising SEQ ID NOs: 2 and 3.

The amplicon corresponding to the NMUR2 locus obtained by PCR can be sequenced using a sequencing primer comprising SEQ ID NO: 4. A skilled artisan can design a sequencing primer other than SEQ ID NO: 4 to sequence the NMUR2 locus based on the sequences of SEQ ID NOs: 1, 5, and 6 and such embodiments are within the purview of the invention. Alternately, a sequencing primer can be designed based on an adapter introduced into the amplicon by incorporating the adapter into one of the forward and reverse primers used for the PCR amplification.

The sperm specific NMUR2 locus having the sequence of SEQ ID NO: 1 is a locus of 277 base pairs on chromosome 5 and occupies the chromosomal location from chr5: 151784131 to chr1:151784407. The genome coordinates for the NMUR2 locus are chr5:151784131-151784407. The NMUR2 locus contains seven CpG sites that are hypomethylated in the genomes of sperms compared to other cells, particularly, blood cells, vaginal epithelial cells, buccal epithelial cells, or seminal cells other than sperms. Particularly, cytosine residues located at the positions chr5: 151784216 (position 86 of SEQ ID NO: 1), chr5:151784218 (position 88 of SEQ ID NO: 1), chr5:151784223 (position 93 of SEQ ID NO: 1), chr5:151784240 (position 110 of SEQ ID NO: 1), chr5:151784245 (position 115 of SEQ ID NO: 1), chr5:151784252 (cg17433294) (position 122 of SEQ ID NO: 1), and chr5:151784258 (position 128 of SEQ ID NO: 1) are hypomethylated in the NMUR2 genetic locus within the genome of a sperm compared to other cells, particularly, blood cells, vaginal epithelial cells, buccal epithelial cells or seminal cells other than sperms.

In another embodiment, identifying sperms based on the methods provided herein is performed by determining the DNA methylation level at a sperm specific locus, the UBE2U locus. Determining DNA methylation at the UBE2U locus can be performed using a specific primer pair that amplifies from the bisulfite-treated genomic DNA at the UBE2U locus, which has the sequence of SEQ ID NO: 7. An amplicon corresponding to the UBE2U locus can be obtained by PCR using bisulfite-treated genomic DNA as a template and a primer pair comprising SEQ ID NOs: 8 and 9.

The amplicon corresponding to the UBE2U locus obtained by PCR can be sequenced using a sequencing primer comprising SEQ ID NO: 10. A skilled artisan can design a sequencing primer other than SEQ ID NO: 10 to sequence the UBE2U locus based on the sequences of SEQ ID NOs: 7, 11, and 12 and such embodiments are within the purview of the invention. Alternately, a sequencing primer can be designed based on an adapter introduced into the amplicon by incorporating the adapter into one of the forward and reverse primers used for the PCR amplification.

The sperm specific UBE2U locus having the sequence of SEQ ID NO: 7 is a locus of 207 base pairs on chromosome 1 and occupies the chromosomal location from chr1: 64669451 to chr1:64669657. The genome coordinates for the UBE2U locus are chr1:64669451-64669657. The UBE2U locus contains three CpG sites that are hypomethylated in the genomes of sperms compared to other cells, particularly, blood cells, vaginal epithelial cells, or buccal epithelial cells. Particularly, cytosine residues located at the positions chr1:64669473 (cg25108325) (position 23 of SEQ ID NO: 7), chr1:64669489 (position 39 of SEQ ID NO: 7), and chr1:64669492 (position 42 of SEQ ID NO: 7) are hypomethylated in the genomes of sperms compared to other cells, particularly, blood cells, vaginal epithelial cells, buccal epithelial cells or seminal cells other than sperms.

In certain embodiments, identifying blood cells based on the methods provided herein is performed by determining the DNA methylation level at a blood cell specific locus, the AHRR locus. Determining DNA methylation at the AHRR locus can be performed through the use of a specific primer pair that amplifies from the bisulfite-treated genomic DNA at the AHRR locus, which has the sequence of SEQ ID NO: 13. An amplicon corresponding to the AHRR locus can be obtained by PCR using bisulfate-treated genomic DNA as template and a primer pair comprising SEQ ID NOs: 14 and 15.

The amplicon corresponding to the AHRR locus obtained by PCR can be sequenced using a sequencing primer comprising SEQ ID NO: 16. A skilled artisan can design a sequencing primer other than SEQ ID NO: 16 to sequence the AHRR locus based on the sequences of SEQ ID NOs: 13, 17, and 18 and such embodiments are within the purview of the invention. Alternately, a sequencing primer can be designed based on an adapter introduced into the amplicon by incorporating the adapter into one of the forward and reverse primers used for the PCR amplification.

The blood cell specific AHRR locus having the sequence of SEQ ID NO: 13 is a locus of 233 base pairs on chromosome 5 and occupies the chromosomal location from chr5: 368763 to chr5:368995. The genome coordinates for the AHRR locus are chr5:368763-chr5:368995. The AHRR locus contains four CpG sites that are hypomethylated in the genome of a blood cell compared to other cells, particularly, sperms, vaginal epithelial cells, buccal epithelial cells, or seminal cells other than sperms. Particularly, cytosine residues located at the positions chr5:368800 (position 38 of SEQ ID NO: 13), chr5:368804 (position 42 of SEQ ID NO: 13), chr5:368821 (position 59 of SEQ ID NO: 13), chr5: 368843 (cg11902777) (position 81 of SEQ ID NO: 13) are hypomethylated in the genome of a blood cell compared to other cells, particularly, sperms, vaginal epithelial cells, buccal epithelial cells or seminal cells other than sperms.

In certain embodiments, identifying buccal epithelial cells based on the methods provided herein is performed by determining the DNA methylation level at a buccal epithelial cell specific locus, the SA-6 locus. Determining DNA methylation at the SA-6 locus can be performed through the use of a specific primer pair that amplifies from the bisulfite-treated genomic DNA at the SA-6 locus, which has the sequence of SEQ ID NO: 19. An amplicon corresponding to the SA-6 locus can be obtained by PCR using bisulfite-treated genomic DNA as template and a primer pair comprising SEQ ID NOs: 20 and 21.

The amplicon corresponding to the SA-6 locus obtained by PCR can be sequenced using a sequencing primer comprising SEQ ID NO: 22. A skilled artisan can design a sequencing primer other than SEQ ID NO: 22 to sequence the SA-6 locus based on the sequences of SEQ ID NOs: 19, 23 and 24 and such embodiments are within the purview of the invention. Alternately, a sequencing primer can be designed based on an adapter introduced into the amplicon by incorporating the adapter into one of the forward and reverse primers used for the PCR amplification.

The buccal epithelial cell specific SA-6 locus having the sequence of SEQ ID NO: 19 is a locus of 124 base pairs on chromosome 2 and occupies the chromosomal location from chr2:63285615-chr2:63285738. The genome coordinates for the SA-6 locus are chr2:63285615-chr2:63285738. The SA-6 locus contains three CpG sites that are hypermethylated in the genome of a buccal epithelial cell compared to other cells, particularly, sperms, vaginal epithelial cells, blood cells, or seminal cells other than sperms. Particularly, cytosine residues located at the positions chr2:63285645 (position 31 of SEQ ID NO: 19), chr2:63285654 (position 40 of SEQ ID NO: 13), and chr2:63285682 (position 68 of SEQ ID NO: 19), are hypermethylated in the genome of a buccal epithelial cell compared to other cells, particularly, sperms, vaginal epithelial cells, blood cells, or seminal cells other than sperms.

The methods described herein can be practiced with minute amounts of genomic DNA, for example, between 1 ng to 50 ng, particularly, between 5 ng to 30 ng, more particularly, about 20 ng. Moreover, determining the DNA methylation levels at the specific genetic loci described herein, for example, SEQ ID NOs: 1, 7, 13, and 19, can be performed when mixtures of body fluids are present.

Accordingly, one embodiment of the invention provides a method for identifying a sample as containing or not containing a sperm, a buccal epithelial cell, or a blood cell, the method comprising the steps of:

a) determining the DNA methylation levels at the genetic loci corresponding to one or more of SEQ ID NOs: 1, 7, 13, and 19, in:
   i) a genomic DNA isolated from the sample, and
   ii) optionally, a control genomic DNA;
b) optionally, obtaining one or more reference values corresponding to the DNA methylation levels at the genetic loci corresponding to one or more of SEQ ID NOs: 1, 7, 13, and 19; and
c) identifying the sample as:
   i) containing or not containing the sperm based on the DNA methylation level at the genetic locus comprising SEQ ID NO: 1 in the genomic DNA isolated from the sample,
   ii) containing or not containing the sperm based on the DNA methylation level at the genetic locus comprising SEQ ID NO: 7 in the genomic DNA isolated from the sample,
   iii) containing or not containing the blood cell based on the DNA methylation level at the genetic locus comprising SEQ ID NO: 13 in the genomic DNA isolated from the sample, and/or
   iv) containing or not containing the buccal epithelial cell based on the DNA methylation level at the genetic locus comprising SEQ ID NO: 19 in the genomic DNA isolated from the sample.

In one embodiment, the invention provides a method for identifying a sample as containing or not containing, a sperm, the method comprising the steps of:

a) determining the DNA methylation level at the genetic locus comprising SEQ ID NO: 1 in:
   i) a genomic DNA isolated from the sample, and
   ii) optionally, a control genomic DNA;
b) optionally, obtaining one or more reference values corresponding to the DNA methylation level at the genetic locus comprising SEQ ID NO: 1; and
c) identifying the sample as containing or not containing the sperm based on the DNA methylation level at the genetic locus comprising SEQ ID NO: 1 in the genomic DNA isolated from the sample.

In certain such embodiments, the methods further comprise identifying a sample as containing or not containing a sperm, a buccal epithelial cell, or a blood cell, the method comprising the steps of:

a) determining the DNA methylation levels at the genetic loci corresponding to one or more of SEQ ID NOs: 7, 13, and 19, in:
   i) a genomic DNA isolated from the sample, and
   ii) optionally, a control genomic DNA;
b) optionally, obtaining one or more reference values corresponding to the DNA methylation levels at the genetic loci corresponding to one or more of SEQ ID NOs: 7, 13, and 19; and
c) identifying the sample as:
   i) containing or not containing the sperm based on the DNA methylation level at the genetic locus comprising SEQ ID NO: 7 in the genomic DNA isolated from the sample,
   ii) containing or not containing the blood cell based on the DNA methylation level at the genetic locus comprising SEQ ID NO: 13 in the genomic DNA isolated from the sample, and/or
   iii) containing or not containing the buccal epithelial cell based on the DNA methylation level at the genetic locus comprising SEQ ID NO: 19 in the genomic DNA isolated from the sample.

In another embodiment, the invention provides a method for identifying a sample as containing or not containing a sperm, the method comprising the steps of:

a) determining the DNA methylation level at the genetic locus comprising SEQ ID NO: 7 in:
   i) a genomic DNA isolated from the sample, and
   ii) optionally, a control genomic DNA;
b) optionally, obtaining one or more reference values corresponding to the DNA methylation level at the genetic locus comprising SEQ ID NO: 7; and
c) identifying the sample as containing or not containing the sperm based on the DNA methylation level at the genetic locus comprising SEQ ID NO: 7 in the genomic DNA isolated from the sample.

In certain such embodiments, the methods further comprise identifying a sample as containing or not containing one or more of a sperm, a buccal epithelial cell, and a blood cell, the method comprising the steps of:

a) determining the DNA methylation levels at the genetic loci corresponding to one or more of SEQ ID NOs: 1, 13, and 19, in:
   i) a genomic DNA isolated from the sample, and
   ii) optionally, a control genomic DNA;
b) optionally, obtaining one or more reference values corresponding to the DNA methylation levels at the genetic loci corresponding to one or more of SEQ ID NOs: 1, 13, and 19; and
c) identifying the sample as:
   i) containing or not containing the sperm based on the DNA methylation level at the genetic locus comprising SEQ ID NO: 1 in the genomic DNA isolated from the sample,
   ii) containing or not containing the blood cell based on the DNA methylation level at the genetic locus comprising SEQ ID NO: 13 in the genomic DNA isolated from the sample, and/or
   iii) containing or not containing the buccal epithelial cell based on the DNA methylation level at the genetic locus comprising SEQ ID NO: 19 in the genomic DNA isolated from the sample.

In a further embodiment, the invention provides a method for identifying a sample as containing or not containing a blood cell, the method comprising the steps of:

a) determining the DNA methylation level at the genetic locus comprising SEQ ID NO: 13 in:
   i) a genomic DNA isolated from the sample, and
   ii) optionally, a control genomic DNA;
b) optionally, obtaining one or more reference values corresponding to the DNA methylation level at the genetic locus comprising SEQ ID NO: 13; and
c) identifying the sample as containing or not containing the blood cell based on the DNA methylation level at the genetic locus comprising SEQ ID NO: 13 in the genomic DNA isolated from the sample.

In certain such embodiments, the methods further comprise identifying a sample as containing or not containing a sperm or a buccal epithelial cell, the method comprising the steps of:

a) determining the DNA methylation levels at the genetic loci corresponding to one or more of SEQ ID NOs: 1, 7, and 19, in:
   i) a genomic DNA isolated from the sample, and
   ii) optionally, a control genomic DNA;
b) optionally, obtaining one or more reference values corresponding to the DNA methylation levels at the genetic loci corresponding to one or more of SEQ ID NOs: 1, 7, and 19; and
c) identifying the sample as:
   i) containing or not containing the sperm based on the DNA methylation level at the genetic locus comprising SEQ ID NO: 1 in the genomic DNA isolated from the sample,
   ii) containing or not containing the sperm based on the DNA methylation level at the genetic locus comprising SEQ ID NO: 7 in the genomic DNA isolated from the sample, and/or
   iii) containing or not containing the buccal epithelial cell based on the DNA methylation level at the genetic locus comprising SEQ ID NO: 19 in the genomic DNA isolated from the sample.

In an even further embodiment, the invention provides a method for identifying a sample as containing or not containing a buccal epithelial cell, the method comprising the steps of:

a) determining the DNA methylation level at the genetic locus comprising SEQ ID NO: 19 in:
   i) a genomic DNA isolated from the sample, and
   ii) optionally, a control genomic DNA;
b) optionally, obtaining one or more reference values corresponding to the DNA methylation level at the genetic locus comprising SEQ ID NO: 19; and
c) identifying the sample as containing or not containing the buccal epithelial cell based on the DNA methylation level at the genetic locus comprising SEQ ID NO: 19 in the genomic DNA isolated from the sample.

In certain such embodiments, the methods further comprise identifying a sample as containing or not containing a sperm or a blood cell, the method comprising the steps of:

a) determining the DNA methylation levels at the genetic loci corresponding to one or more of SEQ ID NOs: 1, 7, and 13, in:
   i) a genomic DNA isolated from the sample, and
   ii) optionally, a control genomic DNA;
b) optionally, obtaining one or more reference values corresponding to the DNA methylation levels at the genetic loci corresponding to one or more of SEQ ID NOs: 1, 7, and 13; and
c) identifying the sample as:
   i) containing or not containing the sperm based on the DNA methylation level at the genetic locus comprising SEQ ID NO: 1 in the genomic DNA isolated from the sample,
   ii) containing or not containing the sperm based on the DNA methylation level at the genetic locus comprising SEQ ID NO: 7 in the genomic DNA isolated from the sample, and/or
   iii) containing or not containing the blood cell based on the DNA methylation level at the genetic locus comprising SEQ ID NO: 13 in the genomic DNA isolated from the sample.

The control sample used in the methods of the invention can be obtained from one or more of the following: a known vaginal epithelial cell, a known sperm, a known blood cell, a known seminal cell other than sperm, and a known buccal epithelial cell. The control sample can also be a cell other than a vaginal epithelial cell, sperm, blood cell, or buccal epithelial cell and that is known to have the DNA methylation level at the specific genetic loci corresponding to SEQ ID NO: 1 or 7 to be different from the DNA methylation level at the corresponding genetic locus in a sperm cell. The control sample can also be a cell other than a vaginal epithelial cell, sperm, blood cell, or buccal epithelial cell and that is known to have the DNA methylation level at the specific genetic locus corresponding to SEQ ID NO: 13 to be different from the DNA methylation level at the corresponding genetic locus in a blood cell. The control sample can also be a cell other than a vaginal epithelial cell, sperm, blood cell, or buccal epithelial cell and that is known to have the DNA methylation level at the specific genetic locus corresponding to SEQ ID NO: 19 to be different from the DNA methylation level at the corresponding genetic locus in a buccal epithelial cell.

If the control sample is a sperm, the step of identifying the sample as containing the sperm is based on the DNA methylation level at the genetic locus comprising SEQ ID NO: 1 or 7 in the genomic DNA isolated from the sample being similar to the DNA methylation level at the genetic locus comprising SEQ ID NO: 1 or 7 in the control genomic DNA. Also, if the control sample is a sperm, the step of identifying the sample as not containing the sperm is based on the DNA methylation level at the genetic locus comprising SEQ ID NO: 1 or 7 in the genomic DNA isolated from the sample being different from the DNA methylation level at the genetic locus comprising SEQ ID NO: 1 or 7 in the control genomic DNA.

If the control sample is a cell different from a sperm, the step of identifying the sample as containing the sperm is based on the DNA methylation level at the genetic locus comprising SEQ ID NO: 1 or 7 in the genomic DNA isolated from the sample being different from the DNA methylation level at the genetic locus comprising SEQ ID NO: 1 or 7 in the control genomic DNA. Also, if the control sample is a cell different from a sperm, the step of identifying the sample as not containing the sperm is based on the DNA methylation level at the genetic locus comprising SEQ ID NO: 1 or 7 in the genomic DNA isolated from the sample being similar to the DNA methylation level at the genetic locus comprising SEQ ID NO: 1 or 7 in the control genomic DNA.

The reference value corresponding to the DNA methylation level at the genetic locus comprising SEQ ID NO: 1 or 7 can indicate the DNA methylation level at the genetic locus comprising SEQ ID NO: 1 or 7 in a sperm or a cell other than a sperm. As such, the reference value corresponding to the DNA methylation level at the genetic locus comprising SEQ ID NO: 1 or 7 can indicate the presence or absence of a sperm. In a sperm, the NMUR2 genetic locus is methylated at less than about 20%, less than about 15%, less than about 10%, less than about 5%, or less than about 1%. Also, in a sperm, the UBE2U genetic locus is methylated at less than about 20%, less than about 15%, less than about 10%, less than about 5%, or less than about 1%.

Similarly, if the control sample is a blood cell, the step of identifying the sample as containing the blood cell is based on the DNA methylation level at the genetic locus comprising SEQ ID NO: 13 in the genomic DNA isolated from the sample being similar to the DNA methylation level at the genetic locus comprising SEQ ID NO: 13 in the control genomic DNA. Also, if the control sample is a blood cell, the step of identifying the sample as not containing the blood cell is based on the DNA methylation level at the genetic locus comprising SEQ ID NO: 13 in the genomic DNA isolated from the sample being different from the DNA methylation level at the genetic locus comprising SEQ ID NO: 13 in the control genomic DNA.

If the control sample is a cell different from a blood cell, the step of identifying the sample as containing the blood cell is based on the DNA methylation level at the genetic locus comprising SEQ ID NO: 13 in the genomic DNA isolated from the sample being different from the DNA methylation level at the genetic locus comprising SEQ ID NO: 13 in the control genomic DNA. Also, if the control sample is a cell different from a blood cell, the step of identifying the sample as not containing the blood cell is based on the DNA methylation level at the genetic locus comprising SEQ ID NO: 13 in the genomic DNA isolated from the sample being similar to the DNA methylation level at the genetic locus comprising SEQ ID NO: 13 in the control genomic DNA.

The reference value corresponding to the DNA methylation level at the genetic locus comprising SEQ ID NO: 13 can indicate the DNA methylation level at the genetic locus comprising SEQ ID NO: 13 in a blood cell or a cell other than a blood cell. As such, the reference value corresponding to the DNA methylation level at the genetic locus comprising SEQ ID NO: 13 can indicate the presence or absence of a blood cell. In a blood cell, the AHRR genetic locus is methylated at less than about 20%, less than about 15%, less than about 10%, less than about 5%, or less than about 1%.

Further, if the control sample is a buccal epithelial cell, the step of identifying the sample as containing the buccal epithelial cell is based on the DNA methylation level at the genetic locus comprising SEQ ID NO: 19 in the genomic DNA isolated from the sample being similar to the DNA methylation level at the genetic locus comprising SEQ ID NO: 19 in the control genomic DNA. Also, if the control sample is a buccal epithelial cell, the step of identifying the sample as not containing the buccal epithelial cell is based on the DNA methylation level at the genetic locus comprising SEQ ID NO: 19 in the genomic DNA isolated from the sample being different from the DNA methylation level at the genetic locus comprising SEQ ID NO: 19 in the control genomic DNA.

If the control sample is a cell different from a buccal epithelial cell, the step of identifying the sample as containing the buccal epithelial cell is based on the DNA methylation level at the genetic locus comprising SEQ ID NO: 19 in the genomic DNA isolated from the sample being different from the DNA methylation level at the genetic locus comprising SEQ ID NO: 19 in the control genomic DNA. Also, if the control sample is a cell different from a buccal epithelial cell, the step of identifying the sample as not containing the buccal epithelial cell is based on the DNA methylation level at the genetic locus comprising SEQ ID NO: 19 in the genomic DNA isolated from the sample being similar to the DNA methylation level at the genetic locus comprising SEQ ID NO: 19 in the control genomic DNA.

The reference value corresponding to the DNA methylation level at the genetic locus comprising SEQ ID NO: 19 can indicate the DNA methylation level at the genetic locus comprising SEQ ID NO: 19 in a buccal epithelial cell or a cell other than a buccal epithelial cell. As such, the reference value corresponding to the DNA methylation level at the genetic locus comprising SEQ ID NO: 19 can indicate the presence or absence of a buccal epithelial cell. In a buccal epithelial cell, the SA-6 genetic locus is methylated at more than about 60%, more than about 65%, more than about 70%, more than about 80%, or more than about 85%.

In one embodiment, the DNA methylation level of specific genetic loci are used to determine the purity of a cell sample comprising or consisting of one or more of a vaginal epithelial cell, sperm, blood cell, and buccal epithelial cell.

For example, if a sperm sample is obtained, the DNA methylation levels at the NMUR2 and/or the UBE2U loci can be checked in the sample to identify the purity of the sperm sample. For example, if the NMUR2 or the UBE2U genetic locus is about 1-20% methylated, the sperm sample is almost 100% pure; whereas, if the NMUR2 or UBE2U genetic locus is only about 50% methylated, the sperm sample is not pure and may contain at least 30% of other types of cells, particularly, vaginal epithelial cells, blood cells, or buccal epithelial cells.

Similarly, if a blood cell sample is obtained, the DNA methylation level at the AHRR locus can be checked in the sample to identify the purity of the blood cell sample. For example, if the AHRR genetic locus is about 1-20% methylated, the blood cell sample is almost 100% pure; whereas, if the AHRR genetic locus is only about 50% methylated, the blood cell sample is not pure and may contain at least 30% other types of cells, particularly, vaginal epithelial cells, sperms, or buccal epithelial cells.

Moreover, if a buccal epithelial cell sample is obtained, the DNA methylation level at the SA-6 locus can be checked in the sample to identify the purity of the buccal epithelial cell sample. For example, if the SA-6 genetic locus is at least about 60-80% methylated, the buccal epithelial cell sample is almost 100% pure; whereas, if the SA-6 genetic locus is only about 30-40% methylated, the buccal epithelial cell sample is not pure and may contain at least 30% of other types of cells, particularly, vaginal epithelial cells, sperms, or blood cells.

Various techniques are known to a person of ordinary skill in the art to determine the DNA methylation level at the specific loci in a genomic DNA. Non-limiting examples of such techniques include bisulfite conversion, HRM analysis, digestion by restriction enzymes followed by PCR, Combined Bisulfite Restriction Analysis (COBRA), direct sequencing, cloning and sequencing, bisulfite treatment and sequencing, bisulfite treatment and pyrosequencing, mass spectrometry analysis, and probe/microarray based assay. Certain techniques of determining methylation at certain genomic sites are described in Eads et al., Combined bisulfite restriction analysis (COBRA), *Methods Molecular Biology*, 2002; 200:71-85; Xiong Z et al., COBRA: a sensitive and quantitative DNA methylation assay, *Nucleic Acids Research*, 1997, 25:2532-4; Paul et al., Cytosine methylation: quantitation by automated genomic sequencing and GENESCAN analysis, *Biotechniques*, 1996, 21:126-33; Warnecke et al., Identification and resolution of artifacts in bisulfite sequencing, *Methods*, 2002, 27:101-7; Tost et al., Analysis of gene-specific DNA methylation patterns by pyrosequencing technology, *Methods Molecular Biology*, 2007, 373:89-102; and Ehrich et al., Quantitative high-throughput analysis of DNA methylation patterns by base-specific cleavage and mass spectrometry, *Proceedings of the National Academy of Sciences*, 2005; 102:15785-90. Each of these references is herein incorporated by reference its entirety. Additional techniques for determining the DNA methylation level at a genetic locus are known to a person of ordinary skill in the art and such techniques are within the purview of the invention.

In a particular embodiment, the DNA methylation level at the specific locus in a genomic DNA obtained from a sample is determined by HRM analysis. HRM analysis involves bisulfite treatment of genomic DNA. Bisulfite treatment of genomic DNA chemically changes the unmethylated cytosines to uracil, while the methylated cytosines are unchanged. In the PCR reaction using primers designed to amplify a specific locus, uracils are copied as thymines making the PCR product produced from an un-methylated locus thymine-rich, thereby reducing the melting temperature (Tm) of the amplicon compared to the PCR product produced from a methylated locus, which is cytosine-rich. As such, methylation of the specific locus can be determined based on Tm of the amplicon, i.e., higher Tm indicates a methylated locus and lower Tm indicates an un-methylated locus. This technique is referred to as FIRM analysis.

Determining the DNA methylation level at the specific locus in a genomic DNA obtained from a sample by HRM analysis comprises the steps of: obtaining the sample, isolating genomic DNA from the sample, treating the isolated DNA with bisulfite, PCR amplifying the genetic loci using specifically designed primers to produce amplicons corresponding to the genetic loci, determining the melting temperatures of the amplicons produced in the PCR, determining the DNA methylation levels at the specific loci in a genomic DNA based on the melting temperatures of the amplicons. The DNA methylation levels at the specific genetic loci can be used to identify the source of body fluid based on the difference in the melting temperatures of the amplicons produced from the methylated and unmethylated genetic loci.

In one embodiment of the invention, amplification and melt analysis are performed in a single instrument, namely, a real time PCR instrument with melt capacity. Use of a single instrument diminishes the hands-on time making the methods efficient.

In one embodiment, a primer pair designed to amplify the genetic locus after bisulfite treatment of genomic DNA comprising SEQ ID NO: 1 comprises a forward primer comprising SEQ ID NO: 2 and a reverse primer comprising SEQ ID NO: 3. A skilled artisan can design primer pairs other than SEQ ID NOs: 2 and 3 to amplify the NMUR2 genetic locus based on the bisulfite treatment of sequence of SEQ ID NO: 1 and the sequences of the regions flanking the NMUR2 genetic locus in the genomic DNA. Such embodiments are within the purview of the invention.

In another embodiment, a primer pair designed to amplify the genetic locus after bisulfite treatment of genomic DNA comprising SEQ ID NO: 7 comprises a forward primer comprising SEQ ID NO: 8 and a reverse primer comprising SEQ ID NO: 9. A skilled artisan can design primer pairs other than SEQ ID NOs: 8 and 9 to amplify the UBE2U genetic locus based on the bisulfite treatment of sequence of SEQ ID NO: 7 and the sequences of the regions flanking the UBE2U locus in the genomic DNA. Such embodiments are within the purview of the invention.

In a further embodiment, a primer pair designed to amplify the genetic locus comprising SEQ ID NO: 13 comprises a forward primer comprising SEQ ID NO: 14 and a reverse primer comprising SEQ ID NO: 15. A skilled artisan can design primer pairs other than SEQ ID NOs: 14 and 15 to amplify the AHRR genetic locus based on the sequence of SEQ ID NO: 13 and the sequences of regions flanking the AHRR locus in the genomic DNA. Such embodiments are within the purview of the invention.

In another embodiment, a primer pair designed to amplify the genetic locus after bisulfite treatment of genomic DNA comprising SEQ ID NO: 19 comprises a forward primer comprising SEQ ID NO: 20 and a reverse primer comprising SEQ ID NO: 21. A skilled artisan can design primer pairs other than SEQ ID NOs: 20 and 21 to amplify the SA-6 genetic locus based on the bisulfite treatment of sequence of SEQ ID NO: 19 and the sequences of the regions flanking the SA-6 locus in the genomic DNA. Such embodiments are within the purview of the invention.

Accordingly, in one embodiment, the invention provides a method for identifying a sample as containing or not containing one or more human cells selected from a sperm, buccal epithelial cell, and a blood cell, the method comprising the steps of:
  a) isolating genomic DNA from the sample and, optionally, a control sample;
  b) treating the isolated genomic DNA with bisulfite;
  c) PCR amplifying the bisulfite treated genetic loci corresponding to one or more of SEQ ID NOs: 1, 7, 13, and 19 to produce the corresponding one or more amplicons, wherein the PCR amplifying is performed using one or more primer pairs selected from:
    i) SEQ ID NOs: 2 and 3,
    ii) SEQ ID NOs: 8 and 9,
    iii) SEQ ID NOs: 14 and 15, and
    iv) SEQ ID NOs: 20 and 21; and
  d) determining the melting temperatures of the one or more amplicons; and
  e) identifying the sample as:
    i) containing or not containing the sperm based on the melting temperature of the amplicon corresponding to the bisulfite treated genetic locus comprising SEQ ID NO: 1 in the genomic DNA isolated from the sample,
    ii) containing or not containing the sperm based on the melting temperature of the amplicon corresponding to the bisulfite treated genetic locus comprising SEQ ID NO: 7 in the genomic DNA isolated from the sample,
    iii) containing or not containing the blood cell based on the melting temperature of the amplicon corresponding to the genetic locus comprising SEQ ID NO: 13 in the genomic DNA isolated from the sample, and/or
    iv) containing or not containing the buccal epithelial cell based on the melting temperature of the amplicon corresponding to the bisulfite treated genetic locus comprising SEQ ID NO: 19 in the genomic DNA isolated from the sample.

In a specific embodiment, the invention provides a method for identifying a sample as containing or not containing a sperm based on the DNA methylation level of SEQ ID NO: 1 determined using a primer pair comprising SEQ ID NOs: 2 and 3. Such methods can further comprise identifying a sample as containing or not containing a sperm, a blood cell, or a buccal epithelial cell based on the DNA methylation levels of one or more of SEQ ID NOs: 7, 13, and 19 determined using a primer pair comprising SEQ ID NOs: 8 and 9, a primer pair comprising SEQ ID NOs: 14 and 15, and a primer pair comprising SEQ ID NOs: 20 and 21, respectively.

In another embodiment, the invention provides a method for identifying a sample as containing or not containing a sperm based on the DNA methylation level of SEQ ID NO: 7 determined using a primer pair comprising SEQ ID NOs: 8 and 9. Such methods can further comprise identifying a sample as containing or not containing a sperm, a blood cell, or a buccal epithelial cell based on the DNA methylation levels of one or more of SEQ ID NOs: 1, 13, and 19 determined using a primer pair comprising SEQ ID NOs: 2 and 3, a primer pair comprising SEQ ID NOs: 14 and 15, and a primer pair comprising SEQ ID NOs: 20 and 21 respectively.

In a further embodiment, the invention provides a method for identifying a sample as containing or not containing a blood cell based on the DNA methylation level of SEQ ID NO: 13 determined using a primer pair comprising SEQ ID NOs: 14 and 15. Such methods can further comprise identifying a sample as containing or not containing a sperm or a buccal epithelial cell based on the DNA methylation levels of one or both of SEQ ID NOs: 1 and 7 determined using a primer pair comprising SEQ ID NOs: 2 and 3 and a primer pair comprising SEQ ID NOs: 8 and 9, respectively, and the DNA methylation levels of SEQ ID NO: 19 determined using a primer pair comprising SEQ ID NOs: 20 and 21.

In an even further embodiment, the invention provides a method for identifying a sample as containing or not containing a buccal epithelial cell based on the DNA methylation level of SEQ ID NO: 19 determined using a primer pair comprising SEQ ID NOs: 20 and 21. Such methods can further comprise identifying a sample as containing or not containing a sperm or a blood cell based on the DNA methylation levels of one or both of SEQ ID NOs: 1 and 7 determined using a primer pair comprising SEQ ID NOs: 2 and 3 and a primer pair comprising SEQ ID NOs: 8 and 9, respectively, or the DNA methylation levels of SEQ ID NO: 13 determined using a primer pair comprising SEQ ID NOs: 14 and 15.

In one embodiment, the melting temperature of one or more amplicons corresponding to the bisulfite treated genetic loci corresponding to SEQ ID NOs: 1, 7, or 19 is compared to a reference value to determine the DNA methylation level at the genetic loci corresponding to SEQ ID NOs: 1, 7, or 19, which in turn is used to identify the sample as containing or not containing a sperm, or a buccal epithelial cell.

In one embodiment, the melting temperature of between 80° C. and 82° C., particularly, about 80.9° C., for the amplicon corresponding to the bisulfite treated genetic locus comprising SEQ ID NO: 1 is used to identify the presence of a sperm in the sample; whereas, the melting temperature of above 82° C. for the amplicon corresponding to the bisulfite treated genetic locus comprising SEQ ID NO: 1 is used to identify the absence of a sperm in the sample and/or the presence of other body fluids, namely, saliva, blood, semen without sperms, or vaginal secretion.

In another embodiment, the melting temperature of between 76° C. and 78° C., particularly, about 77.1° C., for the amplicon corresponding to the bisulfite treated genetic locus comprising SEQ ID NO: 7 is used to identify the presence of a sperm in the sample; whereas, the melting temperature of above 78° C. for the amplicon corresponding to the bisulfite treated genetic locus comprising SEQ ID NO: 7 is used to identify the absence of a sperm in the sample and/or the presence of other body fluids, namely, saliva, blood, semen without sperms, or vaginal secretion.

In a further embodiment, the melting temperature of between 77° C. and 79° C., particularly, about 77.6° C., for the amplicon corresponding to the bisulfite treated genetic locus comprising SEQ ID NO: 19 is used to identify the presence of a buccal epithelial cell in the sample; whereas, the melting temperature of below 77° C. for the amplicon corresponding to the bisulfite treated genetic locus comprising SEQ ID NO: 19 is used to identify the absence of a buccal epithelial cell in the sample and/or the presence of other body fluids, namely, blood, semen, or vaginal secretion.

The four primer sets described above would amplify genomic DNA isolated from samples containing one or more of vaginal epithelial cells or vaginal secretions, sperms or semen, blood or blood cells, and buccal epithelial cell or saliva. The identification of different body fluids can be made after amplification and further analysis, for example, by HRM analysis or sequencing analysis, such as pyrosequencing analysis.

The primer pairs amplify bisulfite treated genomic DNA regardless of its DNA methylation level and would not amplify genomic DNA that is not bisulfite treated. Therefore, if the DNA sample is not appropriate for PCR amplification, for example, due to a low amount of DNA or presence of impurities, the amplicons will not be produced.

A control DNA sample can be used and treated in the same manner as a test sample to ensure that the reagents are working properly. Therefore, if a test sample fails to produce amplicons, the sample can be identified as a source of a problem for lack of amplification despite having working reagents. Likewise a negative control can be run where, for example, water replaces the genomic DNA to ensure that any amplification is not due to unspecific amplification arising from contaminated reagents.

A control primer pair can also be used that would amplify genomic DNA that is not bisulfite converted. The presence of an amplicon for this primer pair would tell a user that the bisulfite conversion was not successful. Therefore, instead of having an amplification that did not work for an unknown reason, a user would identify a failed bisulfite conversion.

In one embodiment, an amplicon corresponding to a genetic locus is distinguished from other amplicons based on a fluorophore attached to the primer pair designed to amplify the genetic locus. Different fluorophores attached to different primer pairs can be detected at different wavelengths using fluorescence detectors.

In one embodiment, each amplicon is labelled with a fluorophore and different fluorophores are matched with different melt curves. By matching fluorophores with melt curves, the presence of different body fluids in a sample containing a mixture of body fluids can be detected.

In another embodiment, each primer pair is labelled with a fluorophore that is detected at a specific wavelength. As the multiplex PCR proceeds, the fluorophore in the primers is quenched by a nucleotide that specifically binds to the DNA amplicon. Fluorescence decreases with the increase of amplification for that specific locus.

An example of detecting different fluorophores for different primer pairs is provided in the Plexor® qPCR and RT-PCR from Promega, Inc. Certain details of Plexor® qPCR are provided in Technical Manual for Plexor® qPCR (Promega, Literature #TM262, Revised September 2009), the contents of which are herein incorporated by reference in its entirety.

In certain embodiments, a control genomic DNA can comprise DNA that is not bisulfite treated. Therefore, each locus has a "control primer set" directed to a bisulfite untreated genomic DNA sequence and a "test primer sequence" directed to bisulfite treated genomic DNA. Therefore, for every test, one can have a multiplex primer set directed to a bisulfite treated test genomic DNA and a multiplex primer set directed to a bisulfite untreated control genomic DNA.

In a particular embodiment, the DNA methylation level at the specific locus in a genomic DNA obtained from a sample is determined by sequencing, for example, pyrosequencing. Determining methylation of a genetic locus based on sequencing involves bisulfite treating a genomic DNA.

Bisulfite treatment of genomic DNA chemically changes the unmethylated cytosines to uracil, while the methylated cytosines are unchanged. In the PCR reaction using primers designed to amplify a specific bisulfite treated locus, uracils are copied as thymines in an un-methylated site and cytosines are copied as guanines in a methylated site. As such, methylation of the specific site can be determined based on the presence of cytosine in the amplicon; whereas, lack of methylation can be determined based on the presence of cytosine in the amplicon.

Using a sequencing based method, such as pyrosequencing, determining the DNA methylation level at the specific locus in a genomic DNA obtained from a sample by sequencing comprises the steps of: obtaining the sample, isolating genomic DNA from the sample, treating the isolated DNA with bisulfite, PCR amplifying the genetic locus using specifically designed primers to produce an amplicon corresponding to the genetic locus, determining the sequences of the amplicon produced in the PCR, and determining the DNA methylation level at the specific locus in a genomic DNA based on the sequence of the amplicon. The methylation level for a particular CpG site can be determine based on the ratio of C/T at the CpG site. The DNA methylation level at the specific genetic locus can be used to identify the source of body fluid.

Accordingly, in one embodiment, the invention provides a method for identifying a sample as containing or not containing a sperm, a buccal epithelial cell, or a blood cell, the method comprising the steps of:

a) isolating genomic DNA from the sample and, optionally, a control sample;
  b) treating the isolated genomic DNA with bisulfite;
  c) PCR amplifying the genetic loci corresponding to one or more of SEQ ID NOs: 1, 7, 13, and 19 to produce the corresponding one or more amplicons, wherein the PCR amplifying is performed using one or more primer pairs selected from:
    i) SEQ ID NOs: 2 and 3,
    ii) SEQ ID NOs: 8 and 9,
    iii) SEQ ID NOs: 14 and 15, or
    iv) SEQ ID NOs: 20 and 21; and
  d) determining the sequences of the one or more amplicons; and
  e) identifying the sample as:
    i) containing or not containing the sperm based on the sequence of the amplicon corresponding to the bisulfite treated genetic locus comprising SEQ ID NO: 1 in the genomic DNA isolated from the sample,
    ii) containing or not containing the sperm based on the sequence of the amplicon corresponding to the bisulfite treated genetic locus comprising SEQ ID NO: 7 in the genomic DNA isolated from the sample,
    iii) containing or not containing the blood cell based on the sequence of the amplicon corresponding to the bisulfite treated genetic locus comprising SEQ ID NO: 13 in the genomic DNA isolated from the sample, and/or
    iv) containing or not containing the buccal epithelial cell based on the sequence of the amplicon corresponding to the bisulfite treated genetic locus comprising SEQ ID NO: 19 in the genomic DNA isolated from the sample.

The sequencing primer for sequencing the amplicon corresponding to bisulfite treated SEQ ID NO: 1, for example, an amplicon produced in a PCR using a primer pair comprising SEQ ID NOs: 2 and 3, can comprise SEQ ID NO: 4. Accordingly, the step of determining the sequences of the amplicon corresponding to bisulfite treated SEQ ID NO: 1 comprises using the sequencing primer comprising SEQ ID NO: 4. A skilled artisan can design a sequencing primer other than SEQ ID NO: 4 to sequence the NMUR2 locus based on the sequences of SEQ ID NOs: 1, 5, and 6 and such embodiments are within the purview of the invention. Alternately, a sequencing primer can be designed based on an adapter introduced into the amplicon by incorporating the adapter into one of the forward and reverse primers.

The sequencing primer for sequencing the amplicon corresponding to bisulfite treated SEQ ID NO: 7, for example, an amplicon produced in a PCR using a primer pair comprising SEQ ID NOs: 8 and 9, can comprise SEQ ID NO: 10. Accordingly, the step of determining the sequences of the amplicon corresponding to bisulfite treated SEQ ID NO: 7 comprises using the sequencing primer comprising SEQ ID NO: 10. A skilled artisan can design a sequencing primer other than SEQ ID NO: 10 to sequence the UBE2U locus based on the sequences of SEQ ID NOs: 7, 11, and 12 and such embodiments are within the purview of the invention. Alternately, a sequencing primer can be designed based on an adapter introduced into the amplicon by incorporating the adapter into one of the forward and reverse primers.

The sequencing primer for sequencing the amplicon corresponding to bisulfite treated SEQ ID NO: 13, for example, an amplicon produced in a PCR using a primer pair comprising SEQ ID NOs: 14 and 15, can comprise SEQ ID NO: 16. Accordingly, the step of determining the sequences of the amplicon corresponding to bisulfite treated SEQ ID NO: 13 comprises using the sequencing primer comprising SEQ ID NO: 16. A skilled artisan can design a sequencing primer other than SEQ ID NO: 16 to sequence the AHRR locus based on the sequences of SEQ ID NOs: 13, 17, and 18 and such embodiments are within the purview of the invention. Alternately, a sequencing primer can be designed based on an adapter introduced into the amplicon by incorporating the adapter into one of the forward and reverse primers.

The sequencing primer for sequencing the amplicon corresponding to bisulfite treated SEQ ID NO: 19, for example, an amplicon produced in a PCR using a primer pair comprising SEQ ID NOs: 20 and 21, can comprise SEQ ID NO: 22. Accordingly, the step of determining the sequences of the amplicon corresponding to bisulfite treated SEQ ID NO: 19 comprises using the sequencing primer comprising SEQ ID NO: 22. A skilled artisan can design a sequencing primer other than SEQ ID NO: 22 to sequence the SA-6 locus based on the sequences of SEQ ID NOs: 19, 23, and 24 and such embodiments are within the purview of the invention. Alternately, a sequencing primer can be designed based on an adapter introduced into the amplicon by incorporating the adapter into one of the forward and reverse primers.

In one embodiment, the sequence of one or more amplicons corresponding to the bisulfite treated genetic loci corresponding to SEQ ID NOs: 1, 7, 13, and 19 are compared to reference sequences to determine the DNA methylation levels at the genetic loci comprising SEQ ID NOs: 1, 7, 13, and 19, which in turn is used to identify the sample as containing or not containing a sperm, a buccal epithelial cell, or a blood cell.

A skilled artisan can design a sequencing primer to sequence the amplicons corresponding to the bisulfite treated genetic locus comprising SEQ ID NOs: 1, 7, 13, or 19 based on the sequences of these genetic loci and the sequences of the regions flanking these genetic loci in the genomic DNA. Such embodiments are within the purview of the invention.

In another embodiment, a sequencing primer can be designed based on an adapter introduced into the amplicon by incorporating the adapter into one of the forward and reverse primers.

An "adapter" as used herein is a sequence of about 10 to 20 nucleotides that can be introduced into an amplicon by incorporating the adapter into the primer used for the amplification of the amplicon. Once an amplicon contains an adapter sequence, a primer designed based on the sequence of the adapter can be used to sequence the amplicon.

In certain embodiments, the methods described herein to identify a sample as containing or not containing a sperm, a buccal epithelial cell, and/or a blood cell are practiced on a forensic sample to detect the presence of one or more of these cells in the forensic sample. The methods can be practiced on a forensic sample that is processed to separate a cell suspected to be a vaginal epithelial cell, sperm, blood cell, or buccal epithelial cell before the step of isolating and analyzing the genomic DNA. The methods can also be practiced on a forensic sample that is known to contain only vaginal epithelial cells, sperms, semen, blood cells, or buccal epithelial cells or a combination thereof.

Certain embodiments of the invention also provide a method for determining the DNA methylation levels at the genetic loci corresponding to one or more of SEQ ID NOs: 1, 7, 13, and 19, in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the one or more of the genetic loci corresponding to one or more of SEQ ID NOs: 1, 7, 13, and 19, and
  d) analyzing the PCR amplicons produced in step c) to determine the DNA methylation levels at the genetic loci corresponding to one or more of SEQ ID NOs: 1, 7, 13, and 19.

In a specific embodiment, the invention provides a method for determining the DNA methylation level at the genetic locus comprising SEQ ID NO: 1 in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the genetic locus corresponding SEQ ID NO: 1, and
  d) analyzing the PCR amplicon produced in step c) to determine the DNA methylation level at the genetic locus comprising SEQ ID NO: 1.

Certain such embodiments further comprise determining the DNA methylation levels at genetic loci corresponding to one or more of SEQ ID NOs: 7, 13, and 19, in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the one or more of the genetic loci corresponding to SEQ ID NOs: 7, 13, and 19, and
  d) analyzing the PCR amplicons produced in step c) to determine the DNA methylation levels at the genetic loci corresponding to one or more of SEQ ID NOs: 7, 13, and 19.

In another embodiment, the invention provides a method for determining the DNA methylation level at the genetic locus comprising SEQ ID NO: 7 in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the genetic locus corresponding SEQ ID NO: 7, and
  d) analyzing the PCR amplicon produced in step c) to determine the DNA methylation level at the genetic locus comprising SEQ ID NO: 7.

Certain such embodiments further comprise determining the DNA methylation levels at genetic loci corresponding to one or more of SEQ ID NOs: 1, 13, and 19, in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the one or more of the genetic loci corresponding to one or more of SEQ ID NOs: 1, 13, and 19, and
  d) analyzing the PCR amplicons produced in step c) to determine the DNA methylation levels at the genetic loci corresponding to one or more of SEQ ID NOs: 1, 13, and 19.

In a further embodiment, the invention provides a method for determining the DNA methylation level at the genetic locus comprising SEQ ID NO: 13 in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the genetic locus corresponding SEQ ID NO: 13, and
  d) analyzing the PCR amplicon produced in step c) to determine the DNA methylation level at the genetic locus comprising SEQ ID NO: 13.

Certain such embodiments further comprise determining the DNA methylation levels at genetic loci corresponding to one or more of SEQ ID NOs: 1, 7, and 19, in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the one or more of the genetic loci corresponding to one or more of SEQ ID NOs: 1, 7, and 19, and
  d) analyzing the PCR amplicons produced in step c) to determine the DNA methylation levels at the genetic loci corresponding to one or more of SEQ ID NOs: 1, 7, and 19.

In an even further embodiment, the invention provides a method for determining the DNA methylation level at the genetic locus comprising SEQ ID NO: 19 in a genomic DNA from a cell, the method comprising the steps of:
  a) isolating the genomic DNA from the cell,
  b) treating the genomic DNA with bisulfite,
  c) conducting a PCR using the bisulfite treated genomic DNA as a template and one or more primer pairs designed to produce amplicons corresponding to the genetic locus corresponding SEQ ID NO: 19, and d) analyzing the PCR amplicon produced in step c) to determine the DNA methylation level at the genetic locus comprising SEQ ID NO: 19.

Certain such embodiments further comprise determining the DNA methylation levels at genetic loci corresponding to one or more of SEQ ID NOs: 1, 7, and 13, in a genomic DNA from a cell, the method comprising the steps of:
a) isolating the genomic DNA from the cell,
b) treating the genomic DNA with bisulfite,
c) conducting a PCR using the bisulfite treated genomic DNA as a template and one or more primer pairs designed to produce amplicons corresponding to the one or more of the genetic loci corresponding to one or more of SEQ ID NOs: 1, 7, and 13, and
d) analyzing the PCR amplicons produced in step c) to determine the DNA methylation levels at the genetic loci corresponding to one or more of SEQ ID NOs: 1, 7, and 13.

The DNA methylation levels at the one or more genetic loci comprising SEQ ID NOs: 1, 7, 13, and 19 can be determined using HRM analysis or sequencing. The primer pairs and the sequencing primers provided above in the methods of identifying a sample as containing or not containing a sperm, a buccal epithelial cell, or a blood cell can also be used in the methods disclosed herein for determining the DNA methylation levels at the one or more genetic loci comprising SEQ ID NOs: 1, 7, 13, and 19 and such embodiments are within the purview of the instant invention.

A further embodiment of the invention provides a kit comprising one or more primer pairs designed to amplify the genetic loci corresponding to one or more SEQ ID NOs: 1, 7, 13, and 19 in a bisulfite treated human genomic DNA.

In one embodiment, the kit comprises one or more primer pairs selected from:
i) a primer pair comprising SEQ ID NOs: 2 and 3,
ii) a primer pair comprising SEQ ID NOs: 8 and 9,
iii) a primer pair comprising SEQ ID NOs: 14 and 15, and
iv) a primer pair comprising SEQ ID NOs: 20 and 21.

A skilled artisan can design additional primer pairs to amplify the bisulfite treated genetic loci corresponding to one or more SEQ ID NOs: 1, 7, 13, and 19 based on the sequences of these genetic loci and the sequences of flanking regions in the genomic DNA and such embodiments are within the purview of the invention.

In further embodiments, the invention provides a kit comprising:
i) the primer pair comprising SEQ ID NOs: 2 and 3 and a sequencing primer comprising SEQ ID NO: 4,
ii) the primer pair comprising SEQ ID NOs: 8 and 9 and a sequencing primer comprising SEQ ID NO: 10,
iii) the primer pair comprising SEQ ID NOs: 14 and 15 and a sequencing primer comprising SEQ ID NO: 16, and/or
iv) the primer pair comprising SEQ ID NOs: 20 and 21 and a sequencing primer comprising SEQ ID NO: 22.

A specific embodiment of the invention provides a kit comprising:
(a) a primer pair that amplifies in a PCR a DNA sequence consisting of SEQ ID NO: 5 or 6, and optionally,
(b) a sequencing primer that sequences in a sequencing reaction an amplicon produced by a PCR conducted by using the primer pair that amplifies the DNA sequence consisting of bisulfate treated SEQ ID NO: 1,
wherein each primer of the primer pair and, when present, the sequencing primer, has a sequence complementary to the sequence of SEQ ID NO: 5 or 6 and has between 15 and 30 nucleotides.

In certain such embodiments, the primer pair comprises a forward primer comprising SEQ ID NO: 2 and a reverse primer comprising SEQ ID NO: 3 and, when present, the sequencing primer comprises SEQ ID NO: 4.

A further specific embodiment of the invention provides a kit comprising:
(a) a primer pair that amplifies in a PCR a DNA sequence consisting of SEQ ID NO: 11 or 12, and optionally,
(b) a sequencing primer that sequences in a sequencing reaction an amplicon produced by a PCR conducted by using the primer pair that amplifies the DNA sequence consisting of bisulfite treated SEQ ID NO: 7,
wherein each primer of the primer pair and, when present, the sequencing primer, has a sequence complementary to the sequence of SEQ ID NO: 11 or 12 and has between 15 and 30 nucleotides.

In certain such embodiments, the primer pair comprises a forward primer comprising SEQ ID NO: 8 and a reverse primer comprising SEQ ID NO: 9 and, when present, the sequencing primer comprises SEQ ID NO: 10.

An even further specific embodiment of the invention provides a kit comprising:
(a) a primer pair that amplifies in a PCR a DNA sequence consisting of SEQ ID NO: 17 or 18, and optionally,
(b) a sequencing primer that sequences in a sequencing reaction an amplicon produced by a PCR conducted by using the primer pair that amplifies the DNA sequence consisting of bisulfite treated SEQ ID NO: 13,
wherein each primer of the primer pair and, when present, the sequencing primer, has a sequence complementary to the sequence of SEQ ID NO: 17 or 18 and has between 15 and 30 nucleotides.

In certain such embodiments, the primer pair comprises a forward primer comprising SEQ ID NO: 14 and a reverse primer comprising SEQ ID NO: 15 and, when present, the sequencing primer comprises SEQ ID NO: 16.

A further embodiment of the invention provides a kit comprising:
(a) a primer pair that amplifies in a PCR a DNA sequence consisting of SEQ ID NO: 23 or 24, and optionally,
(b) a sequencing primer that sequences in a sequencing reaction an amplicon produced by a PCR conducted by using the primer pair that amplifies the DNA sequence consisting of bisulfite treated SEQ ID NO: 19,
wherein each primer of the primer pair and, when present, the sequencing primer, has a sequence complementary to the sequence of SEQ ID NO: 23 or 24 and has between 15 and 30 nucleotides.

In certain such embodiments, the primer pair comprises a forward primer comprising SEQ ID NO: 20 and a reverse primer comprising SEQ ID NO: 21 and, when present, the sequencing primer comprises SEQ ID NO: 22.

In further embodiments, the kit comprises one or more reagents, for example, reagents for treating a sample, reagents for isolating cells from the sample, reagents for isolating genomic DNA from the sample, reagents for bisulfite treating the genomic DNA, reagents for conducting PCR, reagents for conducting pyrosequencing and reagent for conducting HRM analysis.

As used herein, the singular forms "a," "an," and "the" are intended to include the plural forms as well, unless the context clearly indicates otherwise. Further, to the extent that the terms "including," "includes," "having," "has,"

"with," or variants thereof are used in either the detailed description and/or the claims, such terms are intended to be inclusive in a manner similar to the term "comprising." The transitional terms/phrases (and any grammatical variations thereof) "comprising," "comprises," "comprise," include the phrases "consisting essentially of," "consists essentially of," "consisting," and "consists."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Typically, "about" indicates within a range of 0 to 10% of a given value. For example, when term "about" is used in the context of the number of nucleotides in oligonucleotides; these oligonucleotides contain the stated number of nucleotides with a variation of 0-10% around the value (X±10%). In the context of melting temperatures where the term "about" is used, the melting temperatures are within 0.5° C. of the stated melting temperature.

As used herein, the phrase "DNA methylation level" as applied to a genetic locus refers to whether one or more cytosine residues present in a CpG have or do not have a methylation group. The DNA methylation level refers to the percentage of cells in a sample that do or do not have a methylation group on such cytosines. For example, if 50 cells in a pool of 100 cells contain methylated cytosines at a CpG site, the DNA methylation level at the CpG site is 50%.

A primer pair is a pair of oligonucleotides, each having about 15 to 30 nucleotides, and designed to amplify a specific locus from a template DNA. Similarly, a sequencing primer is an oligonucleotide having about 15 to 30 nucleotides and designed to sequence an amplicon. Guidelines for designing a primer pair to amplify a specific locus in a template DNA and a sequencing primer to sequence an amplicon are well known in the art.

A primer pair designed to amplify a target locus comprises a forward primer and a reverse primer, each having about 15 to 30 nucleotides, and each having a sequence complementary to the sequence towards the end of the target genomic locus. Similarly, a sequencing primer designed to sequence an amplicon has about 15 to 30 nucleotides and has a sequence complementary to a sequence within the target amplicon to be sequenced.

A person of ordinary skill in the art can design a primer pair or a sequencing primer based on the target genetic locus.

A singleplex PCR is a reaction where only one set of primers is used per reaction;

whereas, a multiplex reaction is one that uses multiple primer sets per PCR reaction.

Materials and Methods

Sample Collection:

Forensically relevant body fluid samples were collected from unrelated volunteers. 23 venous blood, 24 saliva (buccal swab), 22 vaginal secretion, and 20 semen samples containing sperms were collected. Freshly ejaculated semen was collected in a plastic cup and then put onto sterile cotton swabs to dry. Venous blood, saliva, and vaginal secretions were collected directly on sterile cotton swabs and allowed to dry at room temperature. All biological samples were acquired from volunteers.

Screening Strategies:

Blood, saliva, semen, and vaginal secretion (n=3 per sample type) were examined to screen candidates of CpG sites located in 12 genomic loci to identify their tissue-specific differentially methylated regions (tDMRs). In this step, candidates of CpG sites were examined by pyrosequencing. The CpG sites that showed differences in their methylated profiles between various body fluids were selected for further DNA methylation analyses by pyrosequencing and HRM analysis. In this study, only four tDMRs were discovered including locations at the NMUR2, UBE2U, SA-6, and AHRR loci.

DNA Extraction and Bisulfite Conversion:

Dried swabs containing various body fluid samples were DNA extracted by either the EZ1® DNA Investigator Kit on the BioRobot® EZ1 automated purification workstation (Qiagen) or by standard organic extraction using phenol-chloroform-isoamyl alcohol (Thermo Fisher Scientific). The extracted DNA was bisulfite-modified using the EpiTect® Fast DNA Bisulfite Kit (Qiagen), which can modify 1 ng to 2 μg of DNA, to convert the unmethylated cytosine to uracil.

Pyrosequencing:

To determine the DNA methylation levels at the potential markers in various body fluid samples, sequencing was carried out by pyrosequencing. First, specific PCR primers and sequencing primer were designed using PyroMark Assay Design 2.0 software (Qiagen Inc. CA) to amplify the bisulfite modified target regions. After screening more than 100 CpG sites across 12 genetic loci, three loci were found to be tissue specific. The three assays located at the NMUR2, UBE2U, SA-6, and AHRR genes were designed to target different numbers of CpG sites (Table 1). The specific locations were next amplified with one member of each PCR primer pair labeled with biotin to produce biotinylated PCR amplicons needed for the downstream pyrosequencing reaction. The target regions were amplified in a singleplex fashion by utilizing the PyroMark® PCR kit (Qiagen) on the GeneAmp® PCR system 9700 (Applied Biosystems, Foster City, Calif.). The PCR reaction was modified to utilize 15 μl reaction volumes based on the total volume specified by the manufacturer's protocol. The PCR products were pyrosequenced using a Pyromark Q24 pyrosequencer (Qiagen) as per the manufacturer's instructions. Pyromark® Q24 software (Qiagen) was used to calculate the percent methylation for each CpG site. The PCR products were pyrosequenced using a Pyromark Q24 pyrosequencer (Qiagen) as per the manufacturer's instructions. Pyromark® Q24 software (Qiagen) was used to calculate the percent methylation for each CpG site. The results were displayed as a pyrogram with the methylation percentage.

TABLE 1

Assays designed to evaluate CpG sites in three different genetic loci.

| Locus | Sequence | | Chr. | CpG no./ Ampl. size | CpG sites analyzed (bold and underlined) |
|---|---|---|---|---|---|
| NMUR2 | Forward | GTGTTGGGTAGGGAG AAGAGTA (SEQ ID NO: 2) | 5 | 7/277 | GCGCGGAACGGG TGTAGGATGGTTA CGTAGCCGTTTTA CGTTGACGGTGG TGATGTTGAGGAT GGAGG (Nucleotides 85 to 151 of SEQ ID NO: 1/5) |
| | Reverse* | CTAACCTCCTAATCC TACTCCTTAAA (SEQ ID NO: 3) | | | |
| | Sequencing | GGGTGTTTTGTAGTT TG (SEQ ID NO: 4) | | | |
| UBE2U | Forward* | GTTTTGAGATTGGGT TGTGAG (SEQ ID NO: 8) | 1 | 3/207 | CGGTATTGTAGTG AAACGTCGTAGA TGAGGAAGTGTTT AAGTTTT (Nucleotides 23 to 67 of SEQ ID NO: 7/11) |
| | Reverse | CACTTTCCCACACTT AATAAACTAATA (SEQ ID NO: 9) | | | |
| | Sequencing | GATTGGGTTGTGAGT (SEQ ID NO: 10) | | | |
| AHRR | Forward | TGGGGTTTTAAGGTT AGGGTG (SEQ ID NO: 14) | 5 | 4/233 | CGAGCGTGTGAT TTTGGTGATCGTA GAGTTTTTTTGAG GTTTTCGGGTTTT GTGATTTTAGAAA GTGGT (Nucleotides 38 to 106 of SEQ ID NO: 13/17) |
| | Reverse* | AATTTCACACTTCCT CACAATACA (SEQ ID NO: 15) | | | |
| | Sequencing | GGTGTGTTTTTTTTGT AGGA (SEQ ID NO: 16) | | | |
| SA-6 | Forward* | AAAATATATAAATTT ATAATTTGGAAAAGT (SEQ ID NO: 20) | 2 | 3/124 | AAACCAATCGTC TTCTTCCCCTACC AAAATAAAAAAC GTCCTTATCGACT TTTCCAAATTATA AATTTATAT (**:Reverse complement of nucleotides 6 to 77 of SEQ ID NO: 19) |
| | Reverse | TCTTCCCTCAAAAAA AAATAAAACTATCC (SEQ ID NO: 21) | | | |
| | Sequencing | CCTAACCCCCAAATA C (SEQ ID NO: 22) | | | |

Chr.: chromosome
*: biotinylated primer
no: numbers
Ampl.: amplicon
**: The sequence provided in the Table for the locus SA-6 is a reverse complement of nucleotides 6 to 77 of SEQ ID NO: 19. Sequencing primer (SEQ ID NO: 22) is designed to sequence the double stranded amplicon produced by PCR amplification of bisulfite treated SA-6 (SEQ ID NO: 19). However, the sequence provided in the Table for the locus SA-6 is presented in the reverse complementary manner because the sequencing primer is designed to sequence the strand having a sequence complementary to the sequence of SEQ ID NO: 19. The sequencing information can be used to sequence the amplicon corresponding to the SA-6 locus and the methylation status of cytosines at positions 31, 40, and 68.?

HRM Analysis:

HRM analysis is a real-time PCR method that utilizes an unlabeled primer pair for amplification and includes an intercalating dye for amplification detection and melt analysis. The samples were PCR amplified using Rotor-gene SYBER Green kit (Qiagen) on a Rotor Gene 6000 real-time instrument (Qiagen). The kit composed of a buffer that consists of SYBER Green I, HotStarTaq plus, and dNTP mix. The amplification reaction was adjusted to 20 µl based on the total volume specified by the manufacturer. PCR amplifications were performed by adding 1 µL of bisulfite modified DNA to a master mix that consisted of 2x Rotor-Gene SYBER Green PCR master mix and 1 µM of each unlabeled forward and reverse primers. The amplifying primers utilized were unlabeled and had the same sequence as that used for pyrosequencing analysis. Custom designed primers were obtained from Integrated DNA Technologies (IDT), Inc. (Coralville, Iowa). PCR cycling was conducted on the GeneAmp® PCR system 9700 (Applied Biosystems, Foster City, Calif.) under the following conditions: 95° C. for 5 min; 45 cycles of 95° C. for 10 s, 59° C. for 16 s, and 72° C. for 10 s. Immediately afterward, melt analysis was performed by increasing the temperature from 65° C. to 95° C. in 0.3° C. increments and detecting fluorescence in the HRM analysis channel. Melt curve analysis was generated and melting temperatures were determined using the Rotor-Gene 6000 series software (version 1.7).

Statistical Analysis:

Statistical analysis was performed on the methylation profiles generated as percent methylation values from pyrosequencing or as melting points from HRM analysis. The average percent methylation value for each CpG site identified was calculated along with the standard deviations for each cell type. A one-way ANOVA with Tukey's test and Wetch test were carried out to determine if there were statistical differences in the percent methylation levels between the four types of body fluids. Methylation differences were considered statistically significant if p-values were 0.05 or less. All the analyses were performed using SPSS statistics software ver. 23.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Designing Primers for Genomic Loci Specific for Body Fluids

A set of 12 body fluid samples including blood, saliva, semen, and vaginal secretions were used for preliminary evaluation of body fluid identification using 20 different probe methylation sites. Pyrosequencing was used to perform the methylation analysis for the preliminary evaluation at the 21 probe sites located at 12 genetic loci. Four genomic locations were found that contained differentially methylated regions that were tissue specific of which two were found to be markers for sperm, one or buccal epithelial cell, and one for blood. These four body fluid markers were further screened using pyrosequencing and HRM analysis.

Figure 2:
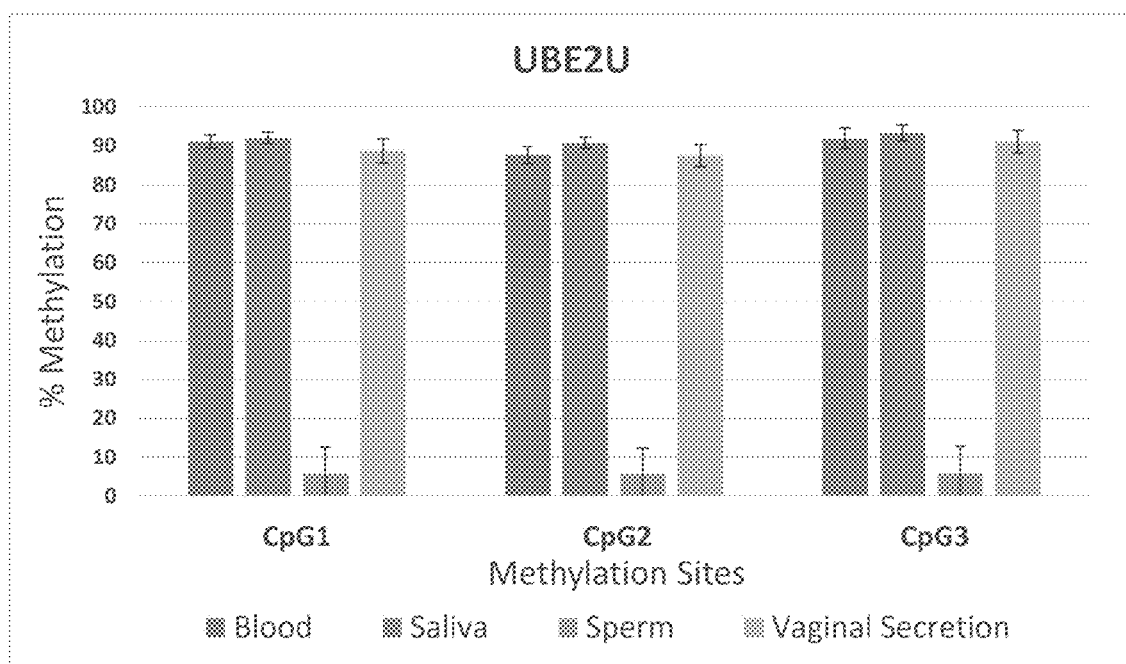
FIG. 2 provides a chart showing the mean percent of methylation on the UBE2U locus determined by pyrosequencing for samples of blood (n=23), saliva (n=24), sperm (n=20), and vaginal secretion (n=22), ±standard deviation of the mean.
Figure 3:
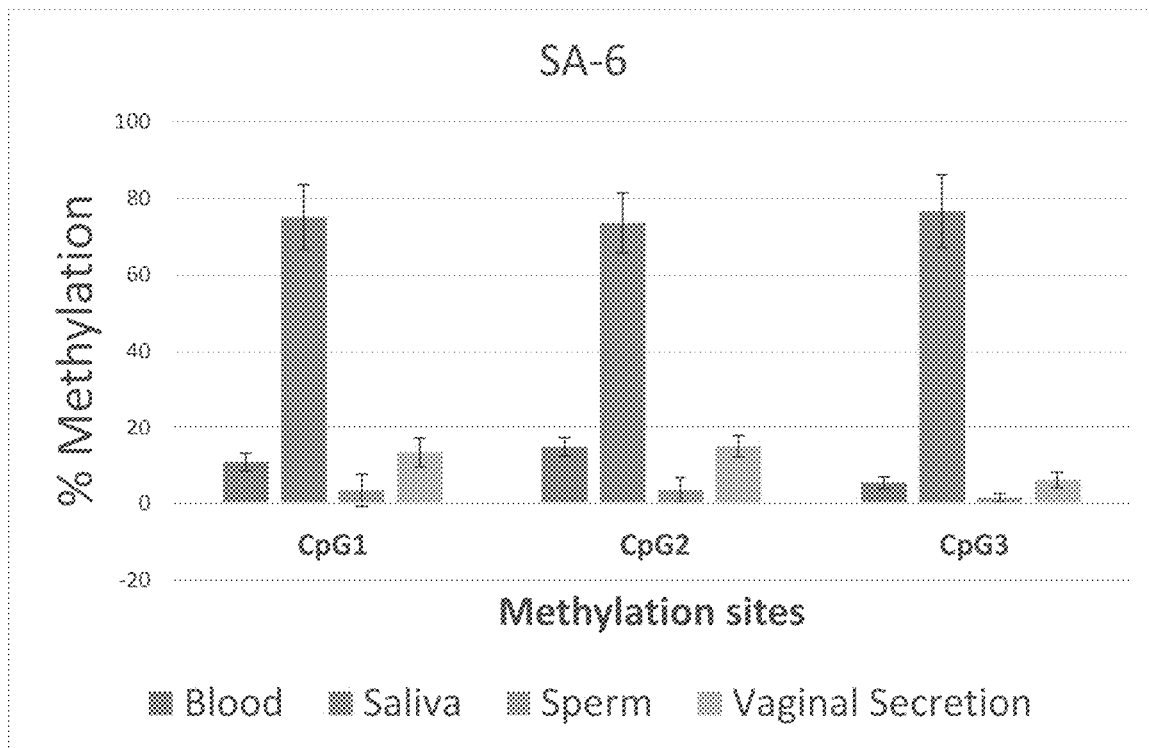
FIG. 3 provides a chart showing the mean percent of methylation using the SA-6 locus determined by pyrosequencing for samples of blood (n=23), saliva (n=24), sperm (n=20), and vaginal secretion (n=21), +/−standard deviation of the mean.

Pyrosequencing Data:

A total of 89 samples were used to further examine the three differentially methylated regions identified including 23 blood, 24 saliva, 20 semen, and 22 vaginal secretion samples. The methylation profiles were successfully analyzed using bisulfite conversion and pyrosequencing. For the loci NMUR2 and UBE2U, sperm presented low percent methylation (less than 20%) whereas the other body fluids had high DNA methylation levels (more than 80%) (FIGS. 1 and 2). Seven CpG sites in the NMUR2 locus showed statistically significant differences between the body fluids and could distinguish semen from other body fluids (Table 2). The UBE2U locus consisted of 3 CpG sites that showed sperm-specific methylation profiles (FIG. 2) and that showed significant difference in methylation levels between sperm and the cells from other body fluids (Table 2). Both of the sperm assays provide effective tools for forensic identification of sperm. Three seminal samples without sperms produced hypermethylation patterns when tested using NMUR2 and UBE2U. The SA-6 maker consisted of 3 CpGs and found to be specific for saliva (FIG. 3). This saliva marker showed statistical significant difference in methylation level between the saliva samples and the other body fluids (Table 2). Using the saliva marker, saliva demonstrated hypermethylated patterns (more than 60%) while the other body fluids showed hypomethylated levels (less than 20%) (FIG. 3). The sperm free seminal samples also showed hypomethylated patterns when tested by the saliva marker. These results confirm that the two sperm markers and the saliva marker and can be very effective tools for forensic identification of sperm and saliva.

Figure 4:
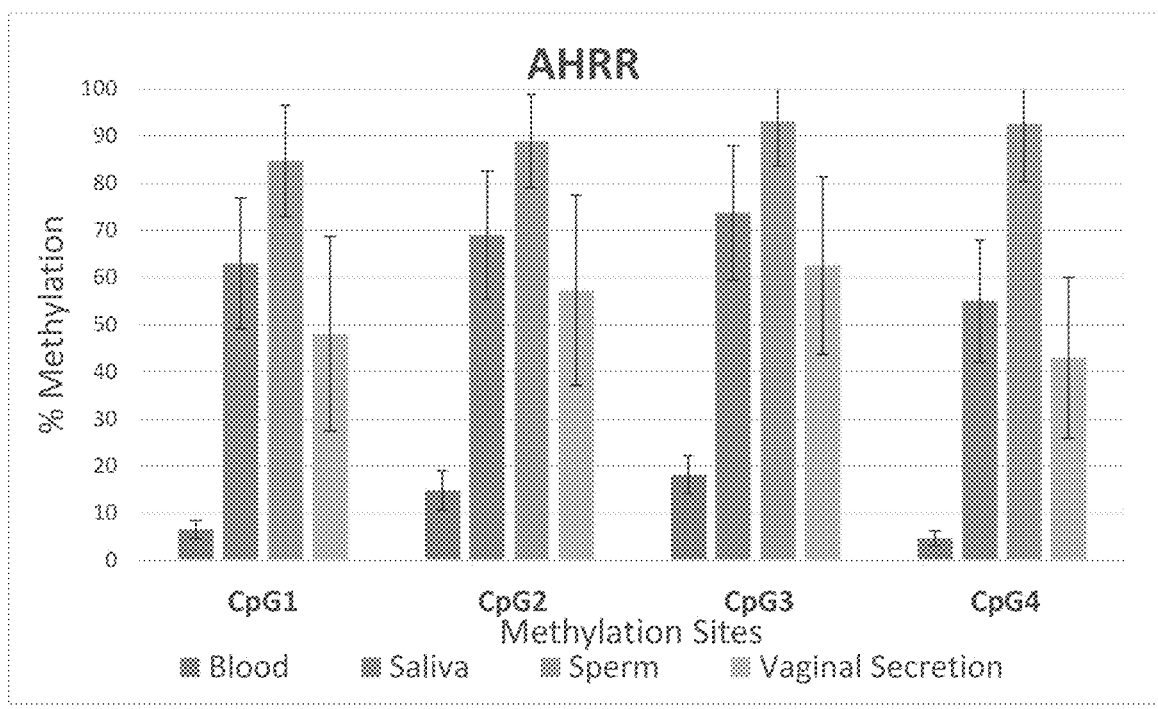
FIG. 4 provides a chart showing the mean percent of methylation on the AHRR locus determined by pyrosequencing for samples of blood (n=23), saliva (n=24), sperm (n=20), and vaginal secretion (n=22), ±standard deviation of the mean.

Similarly, the assay of four CpGs sites at AHHR could also be used as biomarkers for blood identification. At the AHRR gene, blood is hypomethylated compared to other body fluid types, which have low DNA methylation levels (FIG. 4).

TABLE 2

Mean % methylation for the pyrosequencing based assays and mean Tm for the HRM analysis with the significance values based on ANOVA (p-value) and Wetch test (p-value)

| Marker | Body Fluid | CpG (% mean methylation ± standard deviation) | | | | | | | HRM Tm (° C.) |
|---|---|---|---|---|---|---|---|---|---|
| | | CpG1 | CpG2 | CpG3 | CpG4 | CpG5 | CpG6 | CpG7 | All |
| NMUR2 sperm Specific | Semen | 8.6 ± 8.1 | 8.4 ± 7.8 | 8.4 ± 8.1 | 9.0 ± 8.0 | 7.8 ± 7.5 | 8.6 ± 7.3 | 8.4 ± 7.6 | 80.9 ± 0.1 |
| | Vaginal Secretion | 94.8 ± 3.8 | 95.0 ± 3.2 | 94.3 ± 4.0 | 93.5 ± 4.1 | 91.5 ± 3.5 | 92.5 ± 3.2 | 91.6 ± 4.0 | 84.6 ± 0.1 |
| | Saliva | 96.7 ± 0.5 | 96.7 ± 0.6 | 96.1 ± 0.9 | 95.0 ± 1.0 | 92.4 ± 0.9 | 94.4 ± 1.5 | 93.2 ± 0.9 | 84.5 ± 0.2 |
| | Blood | 95.8 ± 1.3 | 95.9 ± 1.3 | 94.4 ± 0.9 | 92.8 ± 1.3 | 87.0 ± 1.7 | 92.5 ± 5.1 | 90.9 ± 2.2 | 84.5 ± 0.2 |
| | p-value | $1.6 \times 10^{-79}$ | $5.5 \times 10^{-82}$ | $5.6 \times 10^{-79}$ | $1.0 \times 10^{-77}$ | $3.2 \times 10^{-74}$ | $3.2 \times 10^{-81}$ | $6.1 \times 10^{-75}$ | $2.0 \times 10^{-83}$ |
| | p-value | $1.1 \times 10^{-33}$ | $2.7 \times 10^{-36}$ | $2.1 \times 10^{-35}$ | $1.2 \times 10^{-34}$ | $1.6 \times 10^{-33}$ | $5.4 \times 10^{-38}$ | $5.6 \times 10^{-33}$ | $3.2 \times 10^{-53}$ |

| UBE2U | | CpG1 | CpG2 | CpG3 | All |
|---|---|---|---|---|---|
| Sperm Specific | Semen | 5.8 ± 6.8 | 5.8 ± 6.6 | 6.0 ± 7.0 | 77.1 ± 0.1 |
| | Vaginal Secretion | 88.8 ± 3.1 | 87.5 ± 2.9 | 91.1 ± 2.9 | 78.8 ± 0.1 |
| | Saliva | 92.1 ± 1.5 | 90.8 ± 1.5 | 93.3 ± 2.0 | 78.8 ± 0.1 |
| | Blood | 91.1 ± 1.3 | 87.6 ± 2.2 | 91.9 ± 2.7 | 78.7 ± 0.1 |
| | p-value | $9.2 \times 10^{-84}$ | $2.1 \times 10^{-83}$ | $4.6 \times 10^{-82}$ | $1.6 \times 10^{-77}$ |
| | p-value | $1.6 \times 10^{-39}$ | $2.2 \times 10^{-39}$ | $7.8 \times 10^{-40}$ | $4.3 \times 10^{-47}$ |

| SA-6 | | CpG1 | CpG2 | CpG3 | All |
|---|---|---|---|---|---|
| Saliva Specific | Sperm | 3.5 ± 4.2 | 3.6 ± 3.2 | 1.45 ± 1.1 | 76.4 ± 0.12 |
| | Vaginal Secretion | 13.3 ± 3.8 | 15 ± 2.8 | 6.2 ± 2.1 | 76.5 ± 0.08 |
| | Saliva | 75 ± 8.5 | 73.5 ± 7.8 | 76.5 ± 9.5 | 77.6 ± 0.05 |
| | Blood | 10.9 ± 2.3 | 14.8 ± 2.4 | 5.5 ± 1.5 | 76.4 ± 0.1 |
| | p-value | $1.59 \times 10^{-63}$ | $5.31 \times 10^{-66}$ | $5.73 \times 10^{-68}$ | $3.38 \times 10^{-43}$ |
| | p-value | $1.86 \times 10^{-32}$ | $7.55 \times 10^{-35}$ | $1.69 \times 10^{-34}$ | $1.04 \times 10^{-37}$ |

TABLE 2-continued

Mean % methylation for the pyrosequencing based assays and mean Tm for the
HRM analysis with the significance values based on ANOVA (p-value) and Wetch test (p-value)

| Marker | Body Fluid | CpG (% mean methylation ± standard deviation) | | | | HRM Tm (° C.) |
|---|---|---|---|---|---|---|
| AHRR | | CpG1 | CpG2 | CpG3 | CpG4 | |
| Blood Specific | Semen | 84.7 ± 11.8 | 88.9 ± 9.8 | 93.1 ± 9.8 | 92.7 ± 12.4 | |
| | Vaginal Secretion | 48.2 ± 20.6 | 57.3 ± 20.1 | 62.5 ± 18.8 | 42.9 ± 17.1 | |
| | Saliva | 63.0 ± 13.9 | 69.0 ± 13.6 | 73.7 ± 14.2 | 55.0 ± 12.9 | |
| | Blood | 6.5 ± 1.9 | 14.8 ± 4.2 | 18.1 ± 4.0 | 4.7 ± 1.6 | |
| | p-value | $2.2 \times 10^{-31}$ | $5.5 \times 10^{-31}$ | $3.1 \times 10^{-32}$ | $4.4 \times 10^{-37}$ | |
| | p-value | $1.2 \times 10^{-26}$ | $1.4 \times 10^{-28}$ | $4.3 \times 10^{-29}$ | $3.0 \times 10^{-27}$ | |

HRM Analysis Data

Figure 5:
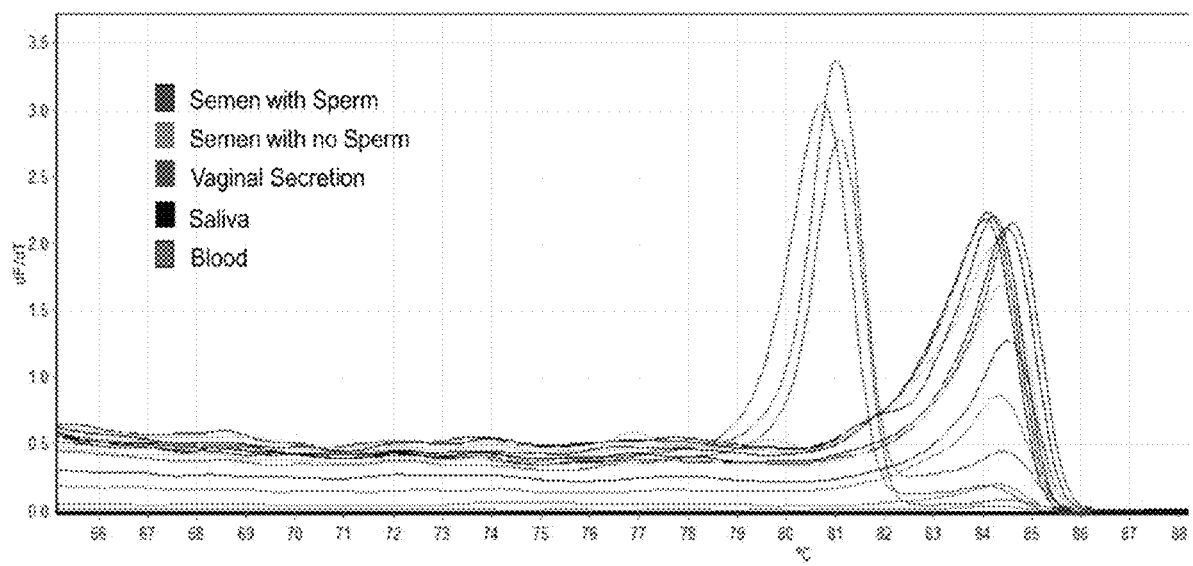
FIG. 5 provides melt curves from samples amplified and analyzed for the NMUR2 locus showing that the melting temperatures for semen containing sperms is lower than those of other body fluids (semen with no sperms, vaginal secretion, blood, and saliva) (n=3 for each sample).
Figure 6:
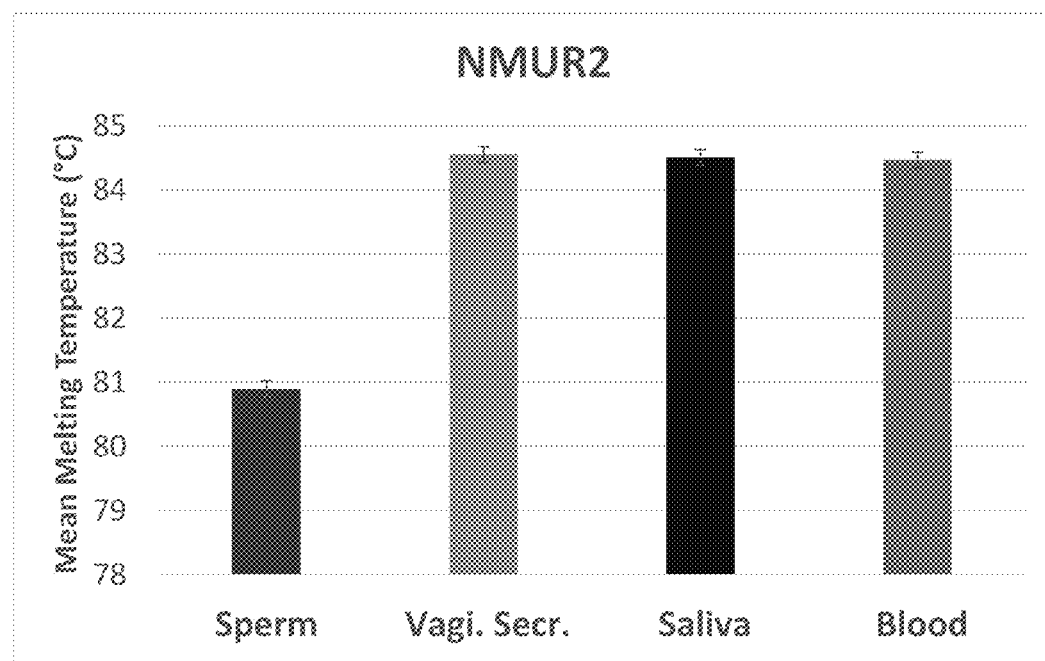
FIG. 6 provides a graph showing the mean values for melting temperatures (° C.) for the NMUR2 locus obtained by HRM analysis for samples of sperm (Tm=80.9° C.), vaginal secretion (84.6° C.), saliva (84.5° C.), and blood (84.5° C.), ±standard deviation.

The same set of samples consisting of 80 different body fluid types were also used to determine whether HRM analysis would also be suited to discriminate the methylation profiles of sperm based on CpG markers at NMUR2 and UBE2U. The melt curve representing the derivative slope of fluoresce (−df/dT) over temperature for the NMUR2 marker showed a distinct pattern for sperm samples when compared to other tissues. The melt curve showing the data for differing tissue types at the NMUR2 marker is shown in FIGS. 5 and 6. At the NMUR2, the sperm samples (n=22) had a lower melting temperature averaging (80.9° C.) than those detected for the other tissue types including blood (84.5° C.), saliva (84.5° C.) and vaginal sections (Tm of 84.6° C.) (FIGS. 5 and 6).

Figure 7:
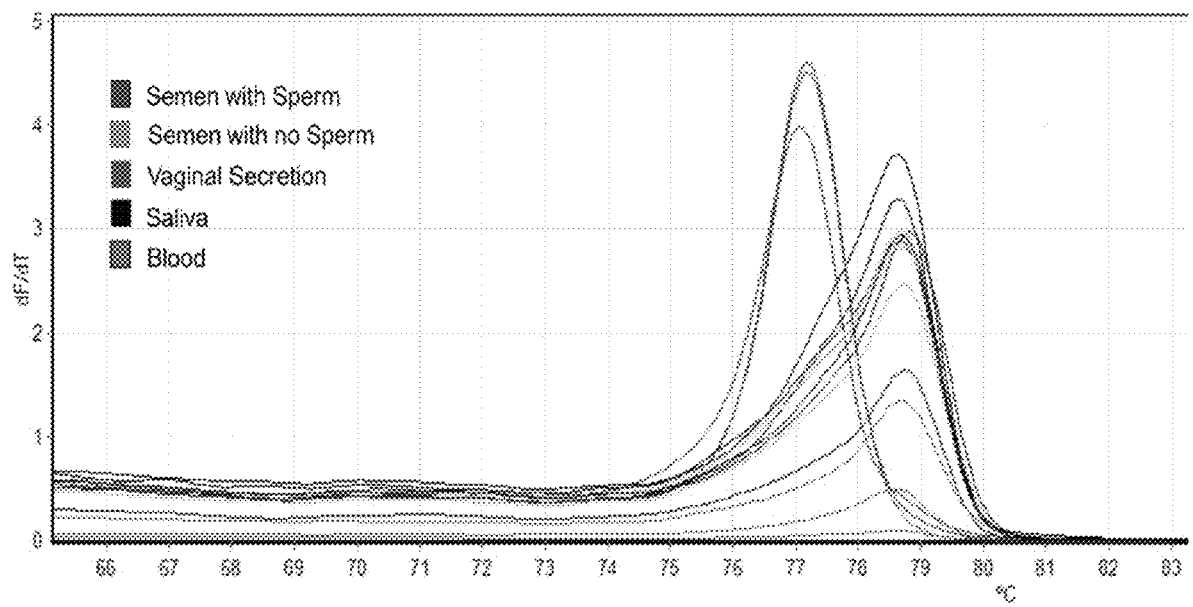
FIG. 7 provides melt curves from samples amplified and analyzed with the UBE2U locus showing that the melting temperatures for semen containing sperms is lower than those of other body fluids (semen with no sperms, vaginal secretion, blood, and saliva) (n=3 for each sample).
Figure 8:
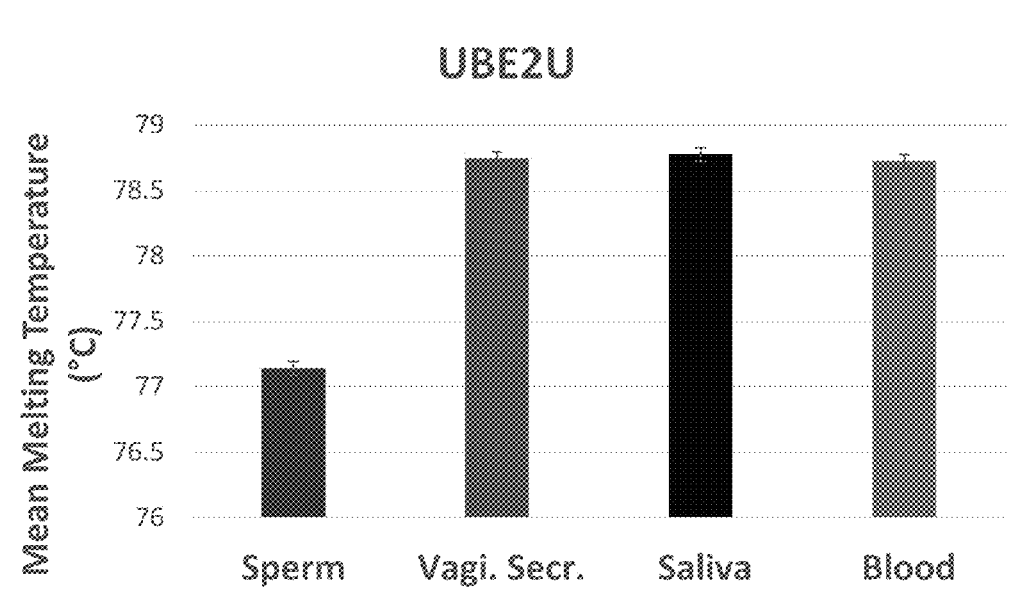
FIG. 8 provides a graph of the mean values for melting temperatures (° C.) for the UBE2U marker obtained by HRM analysis for samples of sperm (n=22, Tm=77.1° C.), vaginal secretion (n=20, Tm=78.7° C.), saliva (n=21, Tm=78.8° C.) and blood (n=20, Tm=78.7° C.), ±standard deviation.
Figure 9:
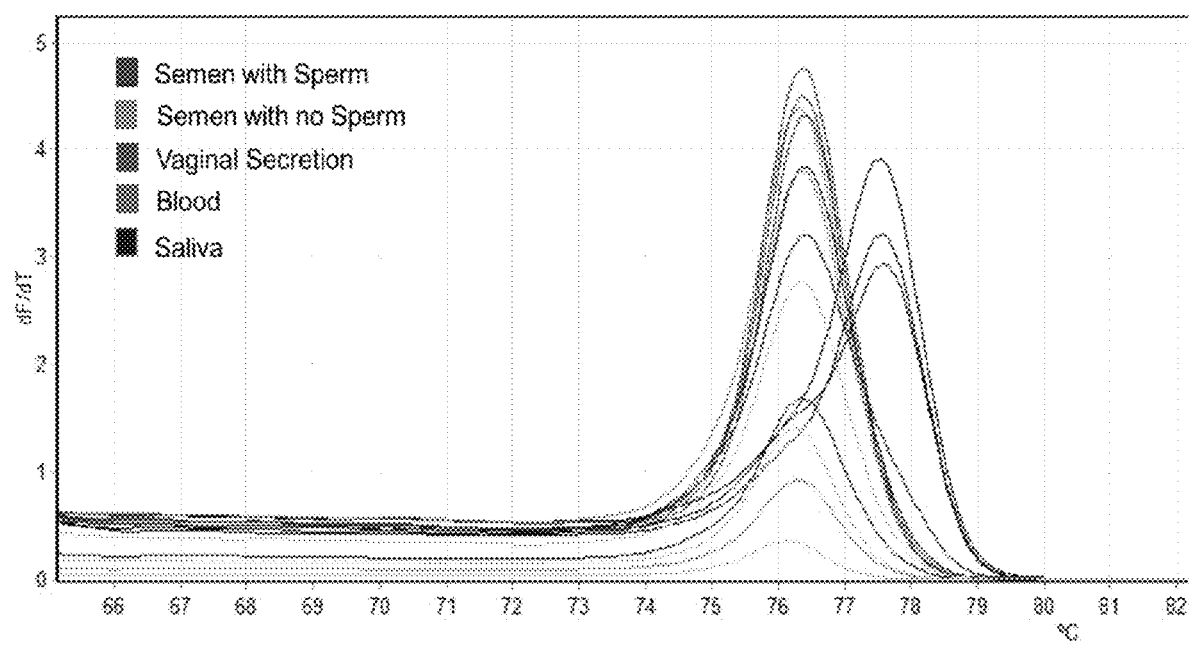
FIG. 9 shows melt curves from samples amplified and analyzed with SA-6 marker showing melting temperatures for saliva samples are higher than the melting temperatures for the samples of the other body fluids (semen with no sperms, semen containing sperms, vaginal secretion, and blood) (n=3 for each sample).
Figure 10:
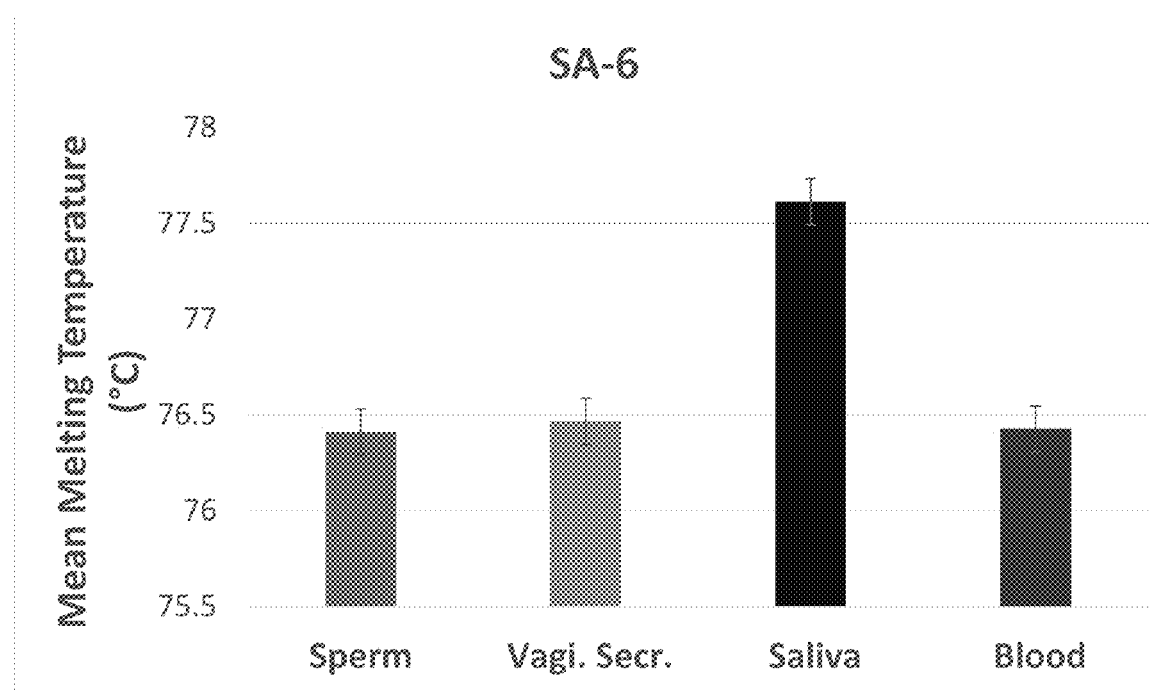
FIG. 10 shows graph for the mean values for melting temperatures (° C.) for SA-6 marker obtained by HRM analysis for saliva samples (n=22, Tm=77.6° C.), vaginal secretion (n=21, Tm=76.5° C.), sperm (n=19, Tm=76.4° C.) and blood (n=21, Tm=76.4° C.), +/−standard deviation.

In the same way, the melting curve for the UBE2U marker also showed distinct pattern of sperm samples compared to other body fluids as illustrated in FIGS. 7 and 8. The melting temperature of sperm samples is lower than the melting temperatures of the other three body fluids. For the UBE2U, the sperm samples (n=22) Tm averaged is 77.1° C. while the other tissue types had higher average melting temperature for blood (Tm=78.7° C., n=20), for saliva (Tm=78.8° C., n=21) and for vaginal secretion (Tm=78.7° C., n=20) (FIG. 8). For the SA-6 marker, the melting temperatures for the saliva samples are higher than the melting temperatures for the cells from other body fluids (FIG. 9). FIG. 10 illustrates that the average Tm is 77.6° C. for saliva samples (n=22) which is higher than the average melting temperature for blood (Tm=76.4° C., n=21), sperm (Tm=76.4° C., n=19) and vaginal secretion (Tm=76.5° C., n=21) (Table 2). However, all four body fluids showed very similar and overlapping melting curves and no distinct pattern can be identified when using the AHRR marker.

Example 2—Determination of the Source Body Fluids Based on the DNA Methylation Levels at Loci Specific for Body Fluids This Example relates to identifying new tDMRs that can be used as biomarkers for forensic body fluid discrimination. Using the discovered tDMR, DNA methylation assays were developed based on pyrosequencing or HRM analysis.

Two novel epigenetic loci, namely NMUR2 and UBE2U, were found to differentiate semen from other body fluids, such as blood, saliva, and vaginal secretion). The AHRR locus was able to distinguished blood from other three tissues using the analysis of methylation signatures of each tissue. In addition, one saliva marker (SA-6) was identified to be saliva specific in which the saliva samples were hypermethylated compared to the other body fluids. Thus, the intergenic region at SA-6 marker located upstream from cg11536474 was able to differentiate saliva while AHRR could distinguish blood from other three body fluids using the analysis of methylation signatures of each body fluid.

Neuromedin U receptor 2 (NMUR2) is a gene that encodes a protein from G-protein coupled receptor 1 family. Such protein serves as a receptor for neuromedin U which is a neuropeptide that is extensively distributed in the gut and central nervous system. This receptor has an important role in regulating food intake and body weight. UBE2U is a protein coding gene for Ubiquitin Conjugating Enzyme E2U. This protein can catalyze the covalent attachment of ubiquitin to other proteins. The genes that encode NMUR2 and UBE2U proteins appear to be very important for semen fluid and its components and not so for the other body fluids tested.

The AHRR gene encodes Aryl-Hydrocarbon Receptor Repressor. This protein is involved in mediating detoxification of harmful substances such as the toxins involved in tobacco smoking. In addition, AHRR is associated with regulation of cell growth and differentiation, the function that correlates with the novel methylation sites identified here that can serve as a blood biomarker. The site at the saliva marker is located at intergenic location upstream from the probe site cg11536474 and is a part of the CpG island promotor region.

The results of testing three seminal fluids from vasectomized male using pyrosequencing and HRM analysis indicate that NMUR2 and the UBE2U are sperm specific. The two sperm markers, NMUR2 and UBE2U, can effectively discriminate semen markers from other body fluids using pyrosequencing (FIGS. 1 and 2). The NMUR2 assay consists of 7 CpG sites, all of which were hypomethylated for sperm while being hypermethylated in other tissues (FIG. 1). The UBE2U assay contains 3 CpG sites that show low DNA methylation level for sperm compared to the other three tissues (FIG. 2). The AHRR blood marker consists of 4 CpG sites that are hypomethylated for blood when compared to other body fluids (FIG. 4).

In general, all CpGs within each of the identified markers present clearly distinguishable DNA methylation levels between the target body fluid and all other body fluids examined, and the differences are statistically significant (p>0.05) (Table 2). Therefore, pyrosequencing provides quantitative results for each individual CpG and permits these markers to be utilized for forensic identification of semen, saliva, and blood samples.

However, if specific methylation values are not required, another quick, simple and inexpensive method to utilize is the HRM analysis. HRM analysis requires only a pair of unlabeled primers and the analysis can be completed in one step. The sperm assay based on NMUR2 produces a melt curve with lower melting temperature for sperm when compared to blood, saliva, semen without sperm, and vaginal secretions. FIGS. 5 and 6 illustrate that DNA from sperm samples presents a melting temperature (Tm) of 80.9° C. with a standard deviation of 0.1° C. which is lower than other body fluids (84.5° C.±0.2 for blood, 84.5° C.±0.2 for saliva, and 84.5° C.±0.1 for vaginal secretion). This indicates that the melting temperatures for sperm samples were approximately 3.6° C. lower than the melting temperatures of the other tissue types.

For the UBE2U assay, sperm also gave a melt curve that had lower melting than the other body fluids. Sperm DNA demonstrated melting temperature averages of 77.1° C. with a standard deviation of 0.1° C., which is lower than other body fluids (78.7° C.±0.1 for blood, 78.8° C.±0.1 for saliva and 78.7° C.±0.1 for vaginal secretions) as shown in FIGS. 7 and 8. This locus showed an approximately 1.6° C. difference in the melting temperature in the sperm samples when compared to the Tm averages of the other tissues. The fact that these two sperm markers are almost entirely hypomethylated means that most of the cytosines were converted into thymines resulting in amplicons with low GC content and low Tms. In SA-6 marker, the average Tm was 77.5° C. (+/−0.05 standard deviation) for saliva DNA whereas other body fluids have lower average Tm (blood was 76.4° C.+/−0.1, sperm was 76.4° C.+/−0.1, and vaginal secretion was 76.5° C.+/−0.08). This indicates that the average Tm for saliva is different by about 1° C. from the other body fluids (FIGS. 9 and 10).

The pyrosequencing data for AHRR marker showed that the DNA methylation level for the blood samples was 18% or below whereas the other body fluids had methylation levels of 48% or above (Table 2 and FIG. 4).

We claim:

1. A method for identifying a sample as containing or not containing a sperm, a buccal epithelial cell, or a blood cell, the method comprising the steps of:
   a) determining the DNA methylation levels at the genetic loci corresponding to one or more of SEQ ID NOs: 1, 7, 13, and 19, in:
      i) a genomic DNA from the sample, and
      ii) optionally, a control genomic DNA,
      through the use of one or more primer pairs selected from:
         i) SEQ ID NOs: 2 and 3,
         ii) SEQ ID NOs: 8 and 9,
         iii) SEQ ID NOs: 14 and 15, and
         iv) SEQ ID NOs: 20 and 21;
   b) optionally, obtaining one or more reference values corresponding to the DNA methylation levels at the genetic loci corresponding to one or more of SEQ ID NOs: 1, 7, 13, and 19; and
   c) identifying the sample as:
      i) containing or not containing the sperm based on the DNA methylation level at the genetic locus comprising SEQ ID NO: 1 in the genomic DNA isolated from the sample,
      ii) containing or not containing the sperm based on the DNA methylation level at the genetic locus comprising SEQ ID NO: 7 in the genomic DNA isolated from the sample,
      iii) containing or not containing the blood cell based on the DNA methylation level at the genetic locus comprising SEQ ID NO: 13 in the genomic DNA isolated from the sample, and/or iv) containing or not containing the buccal epithelial cell based on the DNA methylation level at the genetic locus comprising SEQ ID NO: 19 in the genomic DNA isolated from the sample.

2. The method of claim 1, wherein the sample comprises vaginal epithelial cells, sperms, semen cells other than sperms, blood cells, buccal epithelial cells, or a combination thereof.

3. The method of claim 1, wherein the DNA methylation levels at the specific loci in the genomic DNA obtained from the sample are determined by high-resolution melt (HRM) analysis, wherein the HRM analysis comprises the steps of:
   a) isolating the genomic DNA from the sample and optionally, the control sample;
   b) treating the isolated genomic DNA with bisulfite;
   c) polymerase chain reaction (PCR) amplifying the genetic loci corresponding to one or more of SEQ ID NOs: 1, 7, and 19 to produce the corresponding one or more amplicons,
   d) determining the melting temperatures of the one or more amplicons; and
   e) identifying the sample as:
      i) containing or not containing the sperm based on the melting temperature of the amplicon corresponding to the genetic locus comprising SEQ ID NO: 1 in the genomic DNA isolated from the sample,
      ii) containing or not containing the sperm based on the melting temperature of the amplicon corresponding to the genetic locus comprising SEQ ID NO: 7 in the genomic DNA isolated from the sample, and
      iii) containing or not containing the buccal epithelial cell based on the melting temperature of the amplicon corresponding to the genetic locus comprising SEQ ID NO: 19 in the genomic DNA isolated from the sample.

4. The method of claim 3, wherein PCR amplifying is performed with two or more primers in one reaction.

5. The method of claim 1, wherein the DNA methylation levels at the specific loci in the genomic DNA obtained from the sample are determined by a sequencing analysis, wherein the sequencing analysis comprises the steps of:
   a) isolating the genomic DNA from the sample and optionally, the control sample;
   b) treating the isolated genomic DNA with bisulfite;
   c) PCR amplifying the genetic loci genetic loci corresponding to one or more of SEQ ID NOs: 1, 7, 13, and 19 to produce the corresponding one or more amplicons,
   d) determining the sequences of the one or more amplicons; and
   e) identifying the sample as:
      i) containing or not containing the sperm based on the sequence of the amplicon corresponding to the bisulfite treated genetic locus comprising SEQ ID NO: 1 in the genomic DNA isolated from the sample,
      ii) containing or not containing the sperm based on the sequence of the amplicon corresponding to the bisulfite treated genetic locus comprising SEQ ID NO: 7 in the genomic DNA isolated from the sample,
      iii) containing or not containing the blood cell based on the sequence of the amplicon corresponding to the bisulfite treated genetic locus comprising SEQ ID NO: 13 in the genomic DNA isolated from the sample, and/or
      iv) containing or not containing the buccal epithelial cell based on the sequence of the amplicon corresponding to the bisulfite treated genetic locus comprising SEQ ID NO: 19 in the genomic DNA isolated from the sample.

6. The method of claim 5, wherein the sequencing analysis of the one or more amplicons is performed by a sequencing primer, wherein the sequencing primer is designed based on the sequence of SEQ ID NO: 1, 7, 13, or 19 and/or the sequences of the regions flanking the genetic locus corresponding to the sequence of SEQ ID NO: 1, 7, 13, or 19.

7. The method of claim 5, wherein PCR amplifying is performed with two or more primer pairs in one reaction.

8. The method of claim 5, wherein:
   i) the sequencing analysis of the amplicon corresponding to the bisulfite treated genetic locus comprising SEQ ID NO: 1 is performed using a sequencing primer comprising SEQ ID NO: 4,
   ii) the sequencing analysis of the amplicon corresponding to the bisulfite treated genetic locus comprising SEQ ID NO: 7 is performed using a sequencing primer comprising SEQ ID NO: 10,
   iii) the sequencing analysis of the amplicon corresponding to the bisulfite treated genetic locus comprising SEQ ID NO: 13 is performed using a sequencing primer comprising SEQ ID NO: 16, and/or
   iv) the sequencing analysis of the amplicon corresponding to the bisulfite treated genetic locus comprising SEQ ID NO: 19 is performed using a sequencing primer comprising SEQ ID NO: 22.

9. A method for determining the DNA methylation levels at genetic loci corresponding to one or more of SEQ ID NOs: 1, 7, 13, and 19, in a genomic DNA isolated from a human cell, the method comprising determining the DNA methylation levels at genetic loci by HRM analysis, or determining the DNA methylation levels at genetic loci by a sequencing analysis, using one or more primer pairs selected from:
   i) SEQ ID NOs: 2 and 3,
   ii) SEQ ID NOs: 8 and 9,
   iii) SEQ ID NOs: 14 and 15, and
   iv) SEQ ID NOs: 20 and 21.

10. The method of claim 9, wherein the DNA methylation levels at the specific loci in the genomic DNA obtained from the human cell are determined by HRM analysis, wherein the HRM analysis comprises the steps of:
    a) isolating the genomic DNA from the cell;
    b) treating the isolated genomic DNA with bisulfite;
    c) PCR amplifying the genetic loci corresponding to one or more of SEQ ID NOs: 1, 7, and 19 to produce the corresponding one or more amplicons;
    d) determining the melting temperatures of the one or more amplicons; and
    e) determining the DNA methylation levels at the genetic loci based on the melting temperatures of the one or more amplicons.

11. The method of claim 10, wherein PCR amplifying is performed with two or more primers in one reaction.

12. The method of claim 9, wherein the DNA methylation levels at the specific loci in the genomic DNA obtained from the sample are determined by a sequencing analysis, wherein the sequencing analysis comprises the steps of:
    a) isolating the genomic DNA from the cell;
    b) treating the isolated genomic DNA with bisulfite;
    c) PCR amplifying the genetic loci corresponding to one or more of SEQ ID NOs: 1, 7, 13, and 19 to produce the corresponding one or more amplicons; and
    d) determining the sequences of the one or more amplicons.

13. The method of claim 12, wherein the sequencing analysis is performed by pyrosequencing.

14. The method of claim 13, wherein the sequencing analysis of the one or more amplicons is performed by one or more sequencing primers, wherein the sequencing primers are designed based on the sequences of SEQ ID NO: 1, 7, 13, or 19 and/or the sequences of the regions flanking the genetic loci corresponding to the sequences of SEQ ID NO: 1, 7, 13, or 19.

15. The method of claim 14, wherein:
 i) the sequencing analysis of the amplicon corresponding to the bisulfite treated genetic locus comprising SEQ ID NO: 1 is performed using a sequencing primer comprising SEQ ID NO: 4,
 ii) the sequencing analysis of the amplicon corresponding to the bisulfite treated genetic locus comprising SEQ ID NO: 7 is performed using a sequencing primer comprising SEQ ID NO: 10,
 iii) the sequencing analysis of the amplicon corresponding to the bisulfite treated genetic locus comprising SEQ ID NO: 13 is performed using a sequencing primer comprising SEQ ID NO: 16, and/or
 iv) the sequencing analysis of the amplicon corresponding to the bisulfite treated genetic locus comprising SEQ ID NO: 19 is performed using a sequencing primer comprising SEQ ID NO: 22.

16. The method of claim 3, wherein the PCR amplifying is performed using primer pairs:
 i) SEQ ID NOs: 2 and 3,
 ii) SEQ ID NOs: 8 and 9, and
 iii) SEQ ID NOs: 20 and 21.

17. The method of claim 5, wherein the PCR amplifying is performed using primer pairs:
 i) SEQ ID NOs: 2 and 3,
 ii) SEQ ID NOs: 8 and 9,
 iii) SEQ ID NOs: 14 and 15, and
 iv) SEQ ID NOs: 20 and 21.

18. The method of claim 10, wherein the PCR amplifying is performed using primer pairs:
 i) SEQ ID NOs: 2 and 3,
 ii) SEQ ID NOs: 8 and 9, and
 iii) SEQ ID NOs: 20 and 21.

19. The method of claim 12, wherein the PCR amplifying is performed using primer pairs:
 i) SEQ ID NOs: 2 and 3,
 ii) SEQ ID NOs: 8 and 9,
 iii) SEQ ID NOs: 14 and 15, and
 iv) SEQ ID NOs: 20 and 21.

20. The method of claim 3, wherein each primer pair is labelled with a fluorophore.

* * * * *

```
                        SEQUENCE LISTING

<160> NUMBER OF SEQ ID NOS: 24

<210> SEQ ID NO 1
<211> LENGTH: 277
<212> TYPE: DNA
<213> ORGANISM: Homo sapiens

<400> SEQUENCE: 1
gtgttgggca gggagaagag cacggagaag ccccagacga tgccgaggat cctgagggcc     60
cggcgccggg tgctctgcag tttggcgcgg aacgggtgta ggatggccac gtagcgctcc    120
acgctgacgg tggtgatgct gaggatggag gcgaagcaca cggtctcaaa gagggccgtc    180
ttgaagtagc agcccacggg cccgaacaag aaagggtagt tgcgccacat ctcatagacc    240
tccaggggca ttccaaggag caggaccagg aggtcag                             277

<210> SEQ ID NO 2
<211> LENGTH: 22
<212> TYPE: DNA
<213> ORGANISM: Artificial sequence
<220> FEATURE:
<223> OTHER INFORMATION: primer

<400> SEQUENCE: 2
gtgttgggta gggagaagag ta                                              22

<210> SEQ ID NO 3
<211> LENGTH: 26
<212> TYPE: DNA
<213> ORGANISM: Artificial sequence
<220> FEATURE:
<223> OTHER INFORMATION: primer

<400> SEQUENCE: 3
ctaacctcct aatcctactc cttaaa                                          26

<210> SEQ ID NO 4
<211> LENGTH: 17
<212> TYPE: DNA
<213> ORGANISM: Artificial sequence
<220> FEATURE:
<223> OTHER INFORMATION: primer

<400> SEQUENCE: 4
gggtgttttg tagtttg                                                    17
```

<210> SEQ ID NO 5
<211> LENGTH: 277
<212> TYPE: DNA
<213> ORGANISM: Artificial sequence
<220> FEATURE:
<223> OTHER INFORMATION: amplicon produced after bisulfite treatment

<400> SEQUENCE: 5

```
gtgttgggta gggagaagag tatggagaag ttttagatga tgttgaggat tttgagggtt      60
tggtgttggg tgttttgtag tttggtgtgg aatgggtgta ggatggttat gtagtgtttt     120
atgttgatgg tggtgatgtt gaggatggag gtgaagtata tggttttaaa gagggttgtt     180
ttgaagtagt agtttatggg tttgaataag aaagggtagt tgtgttatat tttatagatt     240
tttaggggta ttttaaggag taggattagg aggttag                              277
```

<210> SEQ ID NO 6
<211> LENGTH: 277
<212> TYPE: DNA
<213> ORGANISM: Artificial sequence
<220> FEATURE:
<223> OTHER INFORMATION: amplicon produced after bisulfite treatment

<400> SEQUENCE: 6

```
gtgttgggta gggagaagag tacggagaag ttttagacga tgtcgaggat tttgagggtt      60
cggcgtcggg tgttttgtag tttggcgcgg aacgggtgta ggatggttac gtagcgtttt     120
acgttgacgg tggtgatgtt gaggatggag gcgaagtata cggttttaaa gagggtcgtt     180
ttgaagtagt agtttacggg ttcgaataag aaagggtagt tgcgttatat tttatagatt     240
tttaggggta ttttaaggag taggattagg aggttag                              277
```

<210> SEQ ID NO 7
<211> LENGTH: 207
<212> TYPE: DNA
<213> ORGANISM: Homo sapiens

<400> SEQUENCE: 7

```
gtcttgagac tgggctgtga gccggcactg cagtgaaacg ccgcagatga ggaagtgccc      60
aagtcttcct tcgggaagtt ctcgtttaga ggagtcagga gaaaagtca ttgttatatc     120 ccaactttag aagccgctta tcttggtacc gttctgaggt tctagaaagc aagtaactta     180
tatcagttta ctaagtgtgg gaaagtg                                         207
```

<210> SEQ ID NO 8
<211> LENGTH: 21
<212> TYPE: DNA
<213> ORGANISM: Artificial sequence
<220> FEATURE:
<223> OTHER INFORMATION: primer

<400> SEQUENCE: 8

```
gttttgagat tgggttgtga g                                                21
```

<210> SEQ ID NO 9
<211> LENGTH: 27
<212> TYPE: DNA
<213> ORGANISM: Artificial sequence
<220> FEATURE:
<223> OTHER INFORMATION: primer

<400> SEQUENCE: 9

```
cactttccca cacttaataa actaata                                          27
```

<210> SEQ ID NO 10
<211> LENGTH: 15
<212> TYPE: DNA
<213> ORGANISM: Artificial sequence
<220> FEATURE:
<223> OTHER INFORMATION: primer

<400> SEQUENCE: 10
gattgggttg tgagt                                                    15

<210> SEQ ID NO 11
<211> LENGTH: 207
<212> TYPE: DNA
<213> ORGANISM: Artificial sequence
<220> FEATURE:
<223> OTHER INFORMATION: amplicon produced after bisulfite treatment

<400> SEQUENCE: 11
gttttgagat tgggttgtga gttggtattg tagtgaaatg ttgtagatga ggaagtgttt    60 aagtttttt ttgggaagtt tttgtttaga ggagttagga gaaaaagtta ttgttatatt   120
ttaattttag aagttgttta ttttggtatt gttttgaggt tttagaaagt aagtaattta   180
tattagttta ttaagtgtgg gaaagtg                                      207

<210> SEQ ID NO 12
<211> LENGTH: 207
<212> TYPE: DNA
<213> ORGANISM: Artificial sequence
<220> FEATURE:
<223> OTHER INFORMATION: amplicon produced after bisulfite treatment

<400> SEQUENCE: 12
gttttgagat tgggttgtga gtcggtattg tagtgaaacg tcgtagatga ggaagtgttt    60 aagtttttt tcgggaagtt ttcgtttaga ggagttagga gaaaaagtta ttgttatatt   120
ttaattttag aagtcgttta ttttggtatc gttttgaggt tttagaaagt aagtaattta   180
tattagttta ttaagtgtgg gaaagtg                                      207

<210> SEQ ID NO 13
<211> LENGTH: 233
<212> TYPE: DNA
<213> ORGANISM: Homo sapiens

<400> SEQUENCE: 13
tggggttcca aggccagggt gtgtttcctc tgcaggacga gcgtgtgact ctggtgaccg    60
cagagccccc ctgaggcccc cgggttctgt gatctcagaa agtggttaga ggcgcattct   120
cttgaccaga gaaacgcgtg ggcactgcca gctgcagcca ccccagtctt cgctggctca   180
gaggaagtgc atttctttgc ggttcatttt gcactgtgag gaagtgtgaa atc         233

<210> SEQ ID NO 14
<211> LENGTH: 21
<212> TYPE: DNA
<213> ORGANISM: Artificial sequence
<220> FEATURE:
<223> OTHER INFORMATION: primer

<400> SEQUENCE: 14
tggggtttta aggttagggt g                                             21

<210> SEQ ID NO 15

```
<211> LENGTH: 24
<212> TYPE: DNA
<213> ORGANISM: Artificial sequence
<220> FEATURE:
<223> OTHER INFORMATION: primer

<400> SEQUENCE: 15
aatttcacac ttcctcacaa taca                                           24

<210> SEQ ID NO 16
<211> LENGTH: 20
<212> TYPE: DNA
<213> ORGANISM: Artificial sequence
<220> FEATURE:
<223> OTHER INFORMATION: primer

<400> SEQUENCE: 16
ggtgtgtttt ttttgtagga                                                20

<210> SEQ ID NO 17
<211> LENGTH: 233
<212> TYPE: DNA
<213> ORGANISM: Artificial sequence
<220> FEATURE:
<223> OTHER INFORMATION: amplicon produced after bisulfite treatment

<400> SEQUENCE: 17
tggggtttta aggttagggt gtgttttttt tgtaggatga gtgtgtgatt ttggtgattg     60
tagagttttt ttgaggtttt tgggttttgt gattttagaa agtggttaga ggtgtatttt    120
tttgattaga gaaatgtgtg ggtattgtta gttgtagtta tttagtttt tgttggttta     180 gaggaagtgt atttttttgt ggtttatttt gtattgtgag gaagtgtgaa att           233

<210> SEQ ID NO 18
<211> LENGTH: 233
<212> TYPE: DNA
<213> ORGANISM: Artificial sequence
<220> FEATURE:
<223> OTHER INFORMATION: amplicon produced after bisulfite treatment

<400> SEQUENCE: 18
tggggtttta aggttagggt gtgttttttt tgtaggacga gcgtgtgatt ttggtgatcg     60
tagagttttt tgaggtttt cgggttttgt gattttagaa agtggttaga ggcgtatttt    120
tttgattaga gaaacgcgtg ggtattgtta gttgtagtta tttagtttt cgttggttta    180 gaggaagtgt atttttttgc ggtttatttt gtattgtgag gaagtgtgaa att           233

<210> SEQ ID NO 19
<211> LENGTH: 124
<212> TYPE: DNA
<213> ORGANISM: Homo sapiens

<400> SEQUENCE: 19
aaaacataca aactcataac ctggaaaagt cgacaaggac gcctttcact ttggcagggg     60
aagaagacga ctggcttgca tctggggtc aggaaggaca gttccatctc cctctgaggg    120
aaga                                                                 124

<210> SEQ ID NO 20
<211> LENGTH: 30
<212> TYPE: DNA
<213> ORGANISM: Artificial sequence
<220> FEATURE:
<223> OTHER INFORMATION: primer
```

```
<400> SEQUENCE: 20
aaaatatata aatttataat ttggaaaagt                                          30

<210> SEQ ID NO 21
<211> LENGTH: 29
<212> TYPE: DNA
<213> ORGANISM: Artificial sequence
<220> FEATURE:
<223> OTHER INFORMATION: primer

<400> SEQUENCE: 21
tcttccctca aaaaaaaata aaactatcc                                           29

<210> SEQ ID NO 22
<211> LENGTH: 16
<212> TYPE: DNA
<213> ORGANISM: Artificial sequence
<220> FEATURE:
<223> OTHER INFORMATION: primer

<400> SEQUENCE: 22
cctaaccccc aaatac                                                         16

<210> SEQ ID NO 23
<211> LENGTH: 124
<212> TYPE: DNA
<213> ORGANISM: Artificial sequence
<220> FEATURE:
<223> OTHER INFORMATION: amplicon produced after bisulfite treatment

<400> SEQUENCE: 23
aaaatatata aatttataat ttggaaaagt tgataaggat gttttttatt ttggtagggg         60
aagaagatga ttggtttgta tttgggggtt aggaaggata gttttatttt tttttgaggg        120
aaga                                                                    124

<210> SEQ ID NO 24
<211> LENGTH: 124
<212> TYPE: DNA
<213> ORGANISM: Artificial sequence
<220> FEATURE:
<223> OTHER INFORMATION: amplicon produced after bisulfite treatment

<400> SEQUENCE: 24
aaaatatata aatttataat ttggaaaagt cgataaggac gttttttatt ttggtagggg         60
aagaagacga ttggtttgta tttgggggtt aggaaggata gttttatttt tttttgaggg        120
aaga                                                                    124
```